(12) United States Patent
Kanamori

(10) Patent No.: US 8,913,113 B2
(45) Date of Patent: *Dec. 16, 2014

(54) IMAGE PROCESSING APPARATUS

(71) Applicant: Panasonic Corporation, Osaka (JP)

(72) Inventor: Katsuhiro Kanamori, Nara (JP)

(73) Assignee: Panasonic Corporation, Osaka (JP)

( * ) Notice: Subject to any disclaimer, the term of this patent is extended or adjusted under 35 U.S.C. 154(b) by 174 days.

This patent is subject to a terminal disclaimer.

(21) Appl. No.: 13/751,329

(22) Filed: Jan. 28, 2013

(65) Prior Publication Data

US 2013/0135453 A1 May 30, 2013

Related U.S. Application Data

(63) Continuation of application No. PCT/JP2011/003932, filed on Jul. 8, 2011.

(30) Foreign Application Priority Data

Sep. 24, 2010 (JP) ................................. 2010-213691

(51) Int. Cl.
*A62B 1/04* (2006.01)
*H04N 7/18* (2006.01)
*A61B 1/00* (2006.01)
*A61B 1/06* (2006.01)
*G02B 5/30* (2006.01)
*G06T 7/00* (2006.01)
*H04N 5/225* (2006.01)

(52) U.S. Cl.
CPC .............. *H04N 7/18* (2013.01); *A61B 1/00009* (2013.01); *A61B 1/00186* (2013.01); *A61B 1/0646* (2013.01); *G02B 5/3025* (2013.01);
(Continued)

(58) Field of Classification Search
CPC ........... A61B 1/00009; A61B 1/00186; A61B 1/00193; A61B 1/0646; G02B 5/3025; G03B 2215/0564; G06T 2207/10068; G06T 2207/30004; G06T 7/0065; H04N 2005/2255; H04N 7/18

USPC .......................................................... 348/65
See application file for complete search history.

(56) References Cited

U.S. PATENT DOCUMENTS 5,914,782 A 6/1999 Sugiyama
2003/0040668 A1 2/2003 Kaneko et al.
(Continued)

FOREIGN PATENT DOCUMENTS

JP 10-104524 A 4/1998
JP 11-313242 A 11/1999
(Continued)

OTHER PUBLICATIONS

International Search Report for corresponding International Application No. PCT/JP2011/003932 mailed Oct. 18, 2011.
(Continued)

*Primary Examiner* — Sath V Perungavoor
*Assistant Examiner* — Dakshesh Parikh
(74) *Attorney, Agent, or Firm* — Renner, Otto, Boisselle & Sklar, LLP

(57) ABSTRACT

In an embodiments, an apparatus includes: a polarized light source which sequentially illuminates an object with three or more plane polarized light rays; and an image sensor which sequentially captures an image of the object that is being illuminated with each plane polarized light ray and which obtains polarization images by sequentially changing the direction of the polarized light transmission axis at each pixel while the object is being illuminated with each polarized light rays. The apparatus further includes: a processing section for generating an intensity maximizing angle image YPH and a degree of intensity modulation image YD; and a distribution estimating section which estimates, based on YPH and YD, the distribution in a single pixel of the azimuth angles of V-grooves on the object's surface.

4 Claims, 26 Drawing Sheets

(52) U.S. Cl.
CPC ........... *A61B 1/00193* (2013.01); *G06T 7/0065* (2013.01); *G03B 2215/0564* (2013.01); *H04N 2005/2255* (2013.01); *G06T 2207/10068* (2013.01); *G06T 2207/30004* (2013.01)
USPC .......................................................... 348/65

(56) References Cited

U.S. PATENT DOCUMENTS

| | | | |
|---|---|---|---|
| 2009/0079982 A1 | 3/2009 | Lefaudeux | |
| 2009/0290039 A1 | 11/2009 | Kanamori et al. | |
| 2010/0079757 A1 | 4/2010 | Murooka et al. | |
| 2010/0102211 A1* | 4/2010 | Murooka et al. | 250/226 |
| 2010/0303344 A1 | 12/2010 | Sato et al. | |
| 2011/0267483 A1 | 11/2011 | Kanamori | |

FOREIGN PATENT DOCUMENTS

| | | |
|---|---|---|
| JP | 2007-086720 A | 4/2007 |
| JP | 4235252 B | 12/2008 |
| JP | 2009-246770 A | 10/2009 |
| JP | 2010-082214 A | 4/2010 |
| JP | 2010-082271 A | 4/2010 |
| JP | 2010-104421 A | 5/2010 |
| JP | 2010-104424 A | 5/2010 |
| JP | 4762369 B | 6/2011 |
| WO | 2010/004677 A1 | 1/2010 |

OTHER PUBLICATIONS

PCT/ISA/237 for corresponding International Application No. PCT/JP2011/003932 dated Oct. 18, 2011 and partial English translation.
Lefaudeux et al., "Compact and robust linear Stokes polarization camera", Proc. of SPIE, vol. 6972, 69720B-1-12, (2008), Polarization: Measurement, Analysis, and Remote Sensing VIII.

* cited by examiner (a)          (b)

(a)

(b)

(c)

IMAGE PROCESSING APPARATUS

This is a continuation of International Application No. PCT/JP2011/003932, with an international filing date of Jul. 8, 2011, which claims priority of Japanese Patent Application No. 2010-213691, filed on Sep. 24, 2010, the contents of which are hereby incorporated by reference.

BACKGROUND

1. Technical Field

The present disclosure relates to an image processing apparatus that can obtain surface topography (micro-geometry) information that surpasses information to be normally obtained by an image sensor from a two-dimensional light intensity image.

2. Description of the Related Art

In the field of endoscopes that capture an image of an organism's organ by irradiating the surface of the organ, which is covered with a semi-transparent mucosa, with light, the surface texture and an image of a blood vessel under the surface need to be checked with regular reflection (i.e., specular reflection) from the surface avoided. To do that, a polarizing endoscope that uses polarized light and polarized image capturing has been proposed. For example, Japanese Laid-Open Patent Publication No. 2009-246770 discloses an endoscope that includes a polarized light source that irradiates an object with light having a particular polarization component and a light receiving section and that generates a shape variation image representing a variation in the surface shape of the object. The light receiving section of that endoscope receives light with a particular polarization component that is included in the light returning from the object and light with a different polarization component from the particular one that is also included in the returning light. The polarization image sensor disclosed in Japanese Laid-Open Patent Publication No. 2009-246770 includes an RGB color mosaic and polarizers, which are arranged so that their polarized light transmission axes face three different directions. Japanese Laid-Open Patent Publication No. 2009-246770 says that to allow the viewer to easily recognize the surface micro-geometry of the mucosa, in particular, a polarization property calculating section calculates a polarization orientation and can generate a two-dimensional distribution of surface tilt information.

SUMMARY

An image processing apparatus according to the present disclosure includes: a polarized light source which sequentially illuminates an object with three or more kinds of plane polarized light rays, of which the planes of polarization have mutually different angles; a polarization image sensor which sequentially captures an image of the object that is being illuminated with each of the three or more kinds of plane polarized light rays and which obtains a plurality of polarization images by sequentially changing the direction of the polarized light transmission axis into three or more different ones at each pixel while the object is being illuminated with each of the three or more kinds of plane polarized light rays; a varying intensity processing section which obtains a relation between the angle of the plane of polarization and the intensity value of each pixel based on a pixel signal supplied from the polarization image sensor, thereby generating an intensity maximizing angle image that is defined by the angle of the plane of polarization that maximizes the intensity value with respect to each said pixel and a degree of intensity modulation image that is defined by the ratio of the amplitude of variation in the intensity value caused by the change of the plane of polarization to an average intensity value with respect to each said pixel; and a distribution estimating section which estimates, based on the intensity maximizing angle image and the degree of intensity modulation image, the distribution in a single pixel of the azimuth angles of V-grooves on the object's surface.

Another image processing apparatus according to the present disclosure includes: a polarized light source which sequentially illuminates an object with three or more kinds of plane polarized light rays, of which the planes of polarization have mutually different angles; a polarization image sensor which sequentially captures an image of the object that is being illuminated with at least one of the three or more kinds of plane polarized light rays and which obtains a plurality of polarization images by sequentially changing the direction of the polarized light transmission axis into three or more different ones at each pixel while the object is being illuminated with at least one of the three or more kinds of plane polarized light rays; and a varying intensity processing section which separates, based on a pixel signal supplied from the polarization image sensor, images representing the light reflected from the object into a surface scattered image and an internally scattered image.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

DETAILED DESCRIPTION

The present inventors discovered via experiments that the polarization image sensor of prior art could not get accurate polarization information on a pixel-by-pixel basis. On top of that, a noticeable moiré pattern would be generated in the polarized image due to interference with the spatial frequency of the object and part of the color mosaic would turn into a polarization mosaic, thus debasing the quality of a full-color image reproduced, too.

The present inventors perfected our invention in order to overcome such a problem and an object of the present invention is to provide, first and foremost, an image processing apparatus that can obtain polarization information on a pixel-by-pixel basis and that can get information about the object's surface micro-geometry within a single pixel based on that polarization information.

An image processing apparatus according to the present disclosure includes a polarized light source which sequentially illuminates an object with three or more kinds of plane polarized light rays, of which the planes of polarization have mutually different angles, and a polarization image sensor which sequentially captures an image of the object that is being illuminated with each of the three or more kinds of plane polarized light rays. That is why information corresponding to an intensity maximizing angle image and a degree of intensity modulation image can be obtained simultaneously with a color image even without developing any special polarization image sensor. Consequently, the image processing apparatus of the present disclosure can estimate the distribution of the grooves' azimuth angles in a single pixel.

Figure 1A:
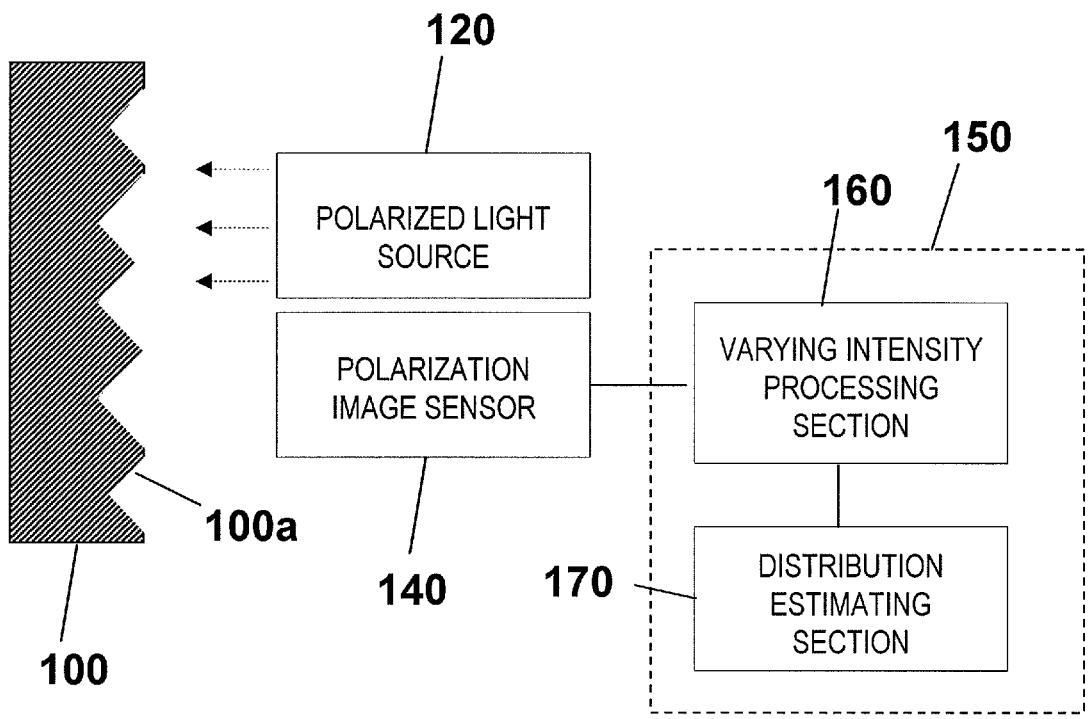
FIG. 1A illustrates an exemplary configuration for an image processing apparatus according to the present disclosure.

As shown in FIG. 1A, an exemplary image processing apparatus according to the present disclosure includes a polarized light source 120, a polarization image sensor 140, a varying intensity processing section 160, and a distribution estimating section 170. The varying intensity processing section 160 and the distribution estimating section 170 are included in an image processing section 150.

The polarized light source 120 sequentially illuminates an object 100 with three or more kinds of plane polarized light rays, of which the planes of polarization have mutually different angles. On the surface of the object 100 of shooting according to the present disclosure, there are multiple grooves 100a. If the object 100 is the surface of an organism's organ, for example, very small grooves are observed on the surface of the object 100. A plane polarized light ray is reflected by the groove 100a on the surface of the object 100 and then incident on the polarization image sensor 140. When the object 100 is being illuminated with each of the three or more kinds of plane polarized light rays, the polarization image sensor 140 shoots the object 100 sequentially. This polarization image sensor 140 obtains a plurality of polarization images by sequentially changing the direction of the polarized light transmission axis into three or more different ones at each pixel while the object 100 is being illuminated with each of those plane polarized light rays. In this description, to "sequentially change the direction of the polarized light transmission axis into three or more different ones at each pixel" means that the polarization direction of a light ray incident on each pixel changes into three or more different ones with time. As will be described later, every pixel may have the same polarized light transmission axis direction or pixels may have multiple different polarized light transmission axis directions. In any case, the point is that while the object 100 is being illuminated with a light ray that is polarized in a certain direction, the polarized light transmission axes of polarizers that are arranged in front of the respective pixels change into three or more different directions.

Figure 1B:
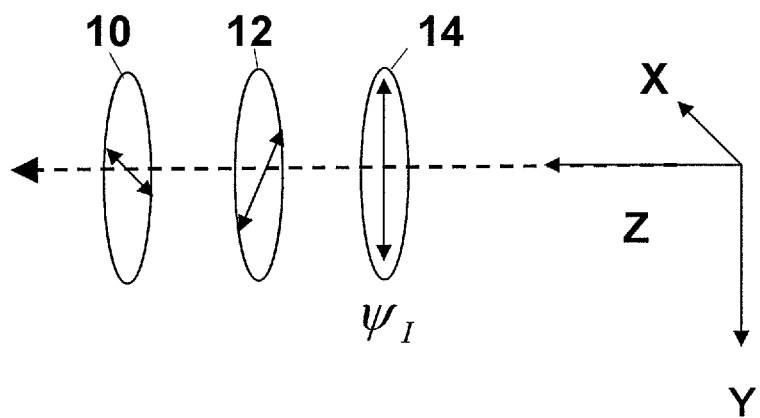
FIG. 1B shows polarization states of a polarized light source.

FIG. 1B is a perspective view schematically showing the polarization directions of three kinds of plane polarized light rays, of which the planes of polarization have mutually different angles. The three polarization states 10, 12 and 14 illustrated in FIG. 1B have planes of polarization that have mutually different angles. Inside each of these circles schematically illustrating the respective polarization states 10, 12 and 14 in FIG. 1B, shown is a double-headed arrow, which indicates the vibration direction of the electric vector that defines the plane of polarization of a plane polarized light ray.

The XYZ coordinates shown in FIG. 1B are of the right-handed system. In this description, the X- and Y-axes are defined in the plane of the image captured by the image sensor 140, and the direction of the Z-axis is defined to be the viewing direction (i.e., the optical axis direction). The plane of polarization of a plane polarized light ray is a plane that is parallel to the vibrating electric vector and that includes the optical axis. If this coordinate system is adopted, the electric vector vibration direction of the plane polarized light ray is parallel to the XY plane. That is why the angle (ψI) of the plane of polarization is defined to be the angle formed by the polarization direction (i.e., the electric vector vibration direction) with respect to the positive X-axis direction. This angle ψI will be described in detail later with reference to FIG. 3.

According to the present disclosure, the polarized light source 120 sequentially illuminates the object 100 with three or more kinds of plane polarized light rays, of which the planes of polarization have mutually different angles. And while the object 100 is being illuminated with each of the three or more kinds of plane polarized light rays, the polarization image sensor 140 shoots the object 100 sequentially.

Now let's go back to FIG. 1A. The varying intensity processing section 160 obtains a relation between the angle of the plane of polarization and the intensity value of each pixel based on a pixel signal supplied from the polarization image sensor 140, thereby generating an "intensity maximizing angle image" and a "degree of intensity modulation image". In this description, the "intensity maximizing angle image" is an image that is defined by the angle of the plane of polarization that maximizes the intensity value with respect to each of the pixels that form the image captured. For example, if the intensity value of a pixel P (x, y) that is defined by a set of coordinates (x, y) becomes maximum when the object 100 is illuminated with a plane polarized light ray, of which the plane of polarization has an angle of 45 degrees, then an intensity maximizing angle of 45 degrees is set with respect to that pixel P (x, y). A single "intensity maximizing angle image" is formed by setting such an intensity maximizing angle value for each pixel. On the other hand, the "degree of intensity modulation image" is an image that is defined by the ratio of the amplitude of variation in the intensity value caused by the change of the plane of polarization to an average intensity value with respect to each pixel. Specifically, if the degree of intensity modulation with respect to a certain pixel P (x, y) is 0.3, then the value of 0.3 is set for that pixel P (x, y). A single "degree of intensity modulation image" is formed by setting such a degree of intensity modulation value for each pixel.

As can be seen, in this description, an "image" refers herein to not only a light intensity image to be directly sensible to human eyes but also any arrangement of numerical values that are allocated to respective pixels. For example, if a single "intensity maximizing angle image" is displayed, the image can be displayed with lightness defined by the intensity maximizing angle value that has been set for each pixel of that intensity maximizing angle image. The intensity maximizing angle image represented in this manner does include a bright and dark pattern that is sensible to human eyes but that is different from an ordinary light intensity image representing the object's intensity. It should be noted that the data itself that represents any of various kinds of "images" will also be sometimes referred to herein as an "image" for the sake of simplicity.

The distribution estimating section 170 shown in FIG. 1A estimates, based on the intensity maximizing angle image and the degree of intensity modulation image, the distribution in a single pixel of the azimuth angles of V-grooves 100a on the object's (100) surface. When the V-groove 100a is viewed straight on, the azimuth angle of a normal to a tilted surface in that V-groove 100a is perpendicular to the direction in which the V-groove 100a runs. If there is one or multiple very small V-grooves 100a in a single pixel, the distribution estimating section 170 according to the present disclosure can estimate the distribution of azimuth angles of the V-grooves 100a on a pixel-by-pixel basis. It will be described in detail later exactly on what principle the distribution estimating section 170 of the present disclosure estimates the distribution of azimuth angles of the V-grooves 100a.

Embodiment 1

Figure 1C:
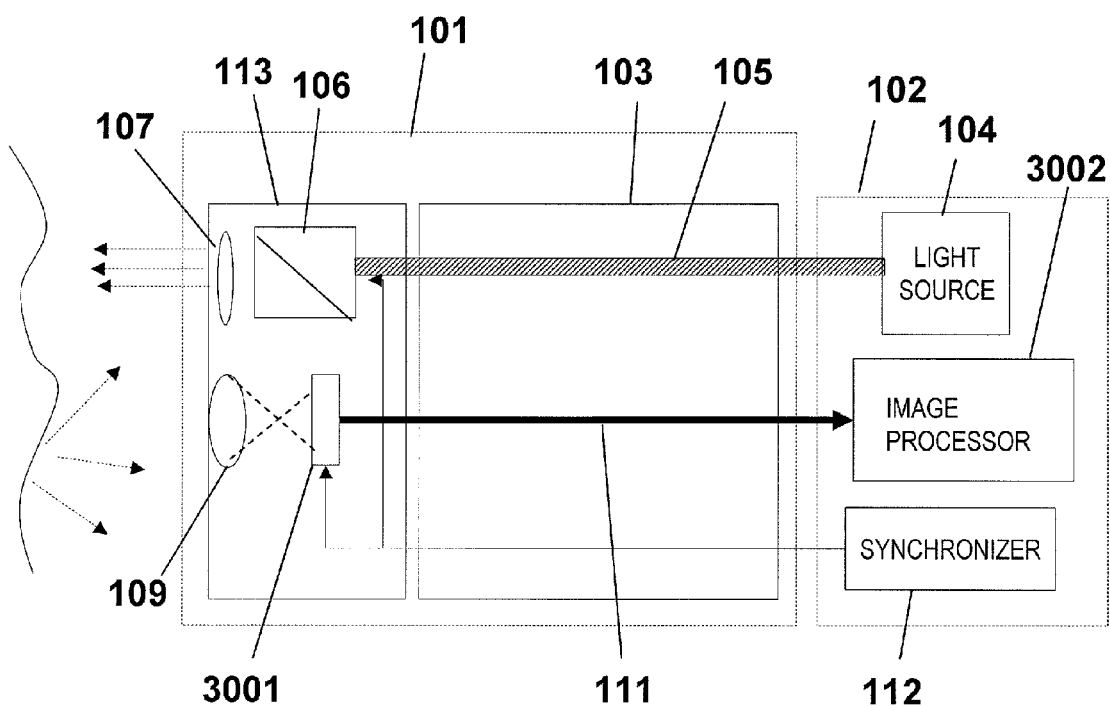
FIG. 1C illustrates a configuration for an image processing apparatus as a first embodiment of the present disclosure.

FIG. 1C schematically illustrates an overall configuration for an image processing apparatus as a first embodiment of the present disclosure.

This image processing apparatus includes an endoscope 101 and a controller 102. The endoscope 101 includes a tip portion 113 with an image capturing sensor and an inserting portion 103 with a light guide 105 and a video signal line 111. As shown in FIG. 1C, the inserting portion 103 of the endoscope 101 has a structure that is elongated horizontally and that can be bent flexibly. Even when bent, the light guide 106 can also propagate light. It should be noted that there are two types of endoscopes, that is, a flexible scope with a flexible inserting portion 103 such as the one of this embodiment and a rigid scope with an inflexible inserting portion. In the rigid scope that is the other type of an endoscope, its inserting portion 103 has a structure for guiding returning light to an image sensor, which is located behind it, using a relay optical system, for example. The present disclosure is applicable to both a flexible scope and a rigid scope.

The controller 102 includes a light source 104, an image processing processor 3002 and a synchronizer 112. The white non-polarized light that has been emitted from the light source 104 is guided through the light guide 105 to a plane of polarization control element 106 of the tip portion 113. The plane of polarization control element 106 may be made up of a polarizer and a liquid crystal element and can transform the non-polarized light into plane polarized light with an arbitrary plane of polarization using a voltage.

The plane of polarization control element 106 is a device that can rotate the plane of polarization using a liquid crystal material. Its exemplary configurations are already disclosed in Japanese Laid-Open Patent Publication No. 11-313242, United States Laid-Open Patent Publication No. 2009/0079982, and Nicolas Lefaudeux, et al., "Compact and Robust Linear Stokes Polarization Camera", Proc. SPIE, Vol. 6972, 69720B, Polarization: Measurement, Analysis, and Remote Sensing VIII (2008) and so on. The plane of polarization control element 106 may be implemented as a voltage application type liquid crystal device that includes a ferroelectric liquid crystal material, a polarization film and a quarter-wave plate in combination. The plane of polarization control element 106 transforms the non-polarized light that has been produced by the light source 104 and then transmitted through the light guide 105 into plane polarized light that has a plane of polarization at an arbitrary angle.

The synchronizer 112 gives the plane of polarization control element 106 an instruction to rotate the plane of polarization, thereby getting the plane of polarization of the illumination rotated. And that polarized illumination is cast toward the object through an illuminating lens 107. At the same time, the synchronizer 112 sends a shooting start signal to an image sensor 3001, thereby getting video. The synchronizer 112 performs this series of processing steps a number of times.

The light returning from the object is transmitted through a shooting lens 109 and then produces an image on the image sensor 3001, the configuration and operation of which will be described later. The video signal representing the image captured is output from the image sensor 3001 and transmitted through the video signal line 111 to reach the image processor 3002. In this embodiment, the polarized light source 120 shown in FIG. 1A is realized by the light source 104, the light guide 105, the plane of polarization control element 106 and the illuminating lens 107. Meanwhile, the polarization image sensor 140 shown in FIG. 1A is realized by the shooting lens 109 and the image sensor 3001. And the varying intensity processing section 160 and the distribution estimating section 170 shown in FIG. 1A are realized by the image processor 3002.

Figure 2:
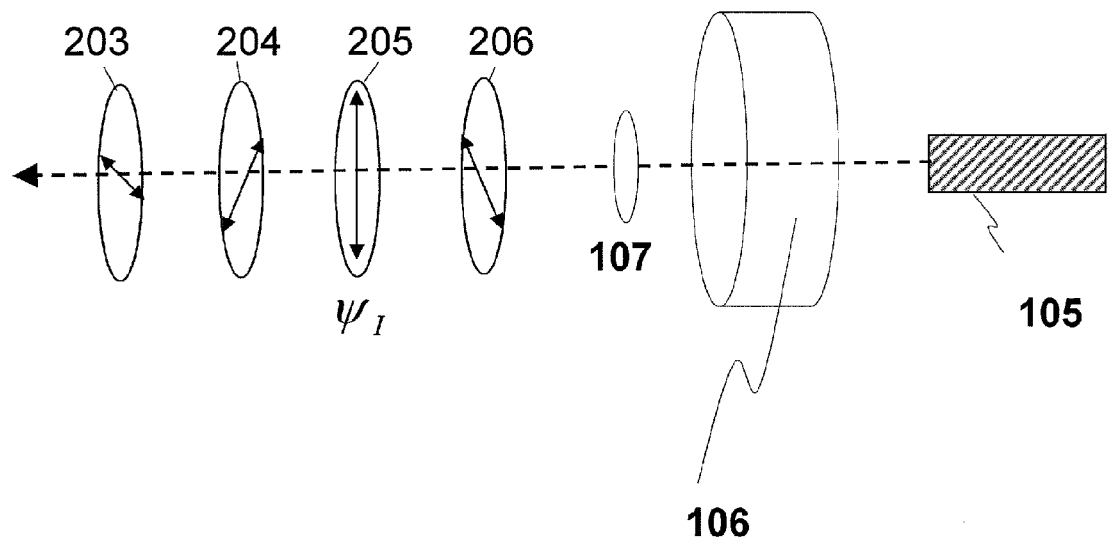
FIG. 2 shows how a plane of polarization control element operates.

Next, it will be described with reference to FIG. 2 how the plane of polarization control element 106 operates.

First, second, third and fourth images are captured in respective states 203, 204, 205 and 206 in which the plane of polarization has an angle of 0, 45, 90 and 135 degrees, respectively. These angles do not always have to be increased on a 45 degree basis. But the angle of increment may also be any other value obtained by dividing 180 degrees by an integer of three or more. If the image sensor has high sensitivity or if the illumination has high illuminance, then the exposure time can be shortened. As a result, the angle of rotation can be set more finely.

According to the prior art references described above, the time it takes to rotate the plane of polarization may be as long as approximately 20 ms when the operating speed is low but may also be as short as 40 to 100 μsec when the operating speed is high. If a high-response-speed liquid crystal material is used and if the sensitivity of the image sensor is increased to a level that is high enough to get an image captured in such a short time, performance that is high enough to shoot a moving picture can be maintained even when the plane of polarization is rotated to those four directions one after another during shooting.

As can be seen easily from FIG. 1C, the optical axis of the illuminating lens 107 is substantially aligned with that of the shooting lens 109. This arrangement is adopted in order to avoid casting shadows on the object as perfectly as possible when the object is monitored with an endoscope.

It should be noted that when an endoscope is used normally, the object should be irradiated with non-polarized light in many cases. According to the present disclosure, by adding together mutually different polarization images as the first through fourth images, for example, a non-polarized average light intensity image can be generated. The present inventors discovered via experiments that when the images represented by multiple polarized light rays, of which the planes of polarization were defined by angles $\psi I$ at regular intervals and which had been radiated toward, and had returned from, the object, were added together, the effect of polarization was canceled and the effect eventually achieved was the same as the one achieved by using a non-polarized light source.

Figure 3:
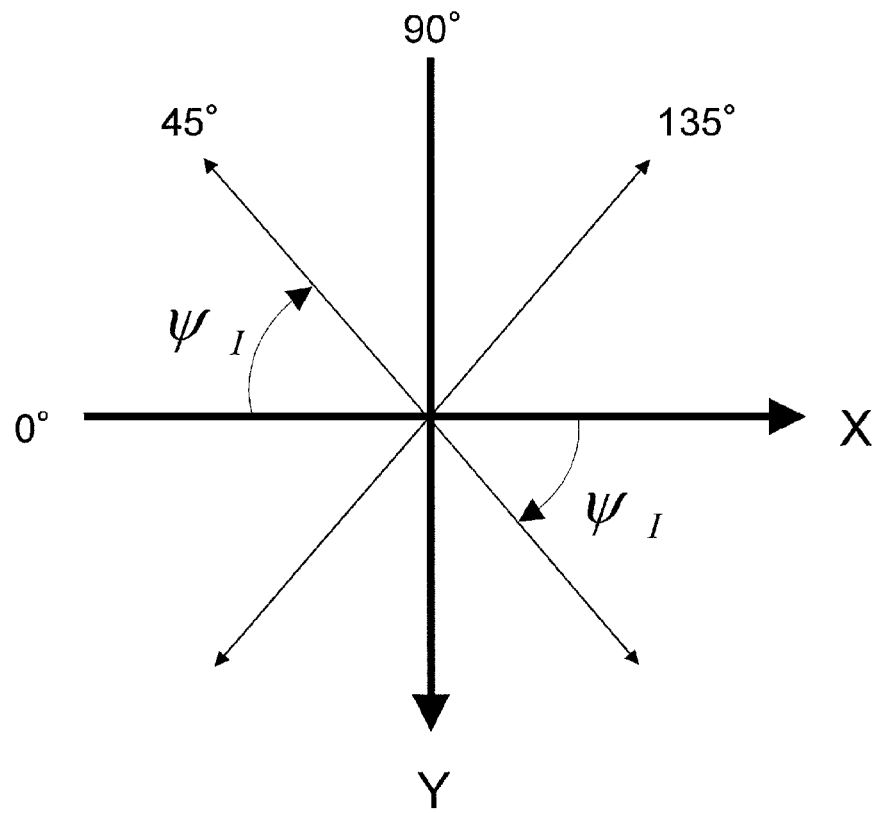
FIG. 3 shows how to define the angle of a plane of polarization.

FIG. 3 shows how the plane of polarization of polarized light source has its angle $\psi I$ defined. As described above, an X-Y coordinate system is defined with respect to the object. In this case, the angle $\psi I$ of the plane of polarization is defined to be positive in the positive Y-axis direction with the negative X-axis direction set to be 0 degrees. If the angle $\psi I$ is saved for reflected light, then the respective planes of polarization of the reflected light and the incident light will have the same angle. And if the angle $\psi I$ of the plane of polarization is going to be increased or decreased, the same polarization state will recur over and over again in a period of 180 degrees. That is to say, a function that uses the angle $\psi I$ of the plane of polarization as a variable is a periodic function that has a period of 180 degrees. In this description, the angle $\psi I$ of the plane of polarization of polarized light source will be sometimes referred to herein as an "incident plane of polarization angle".

Figure 4A:
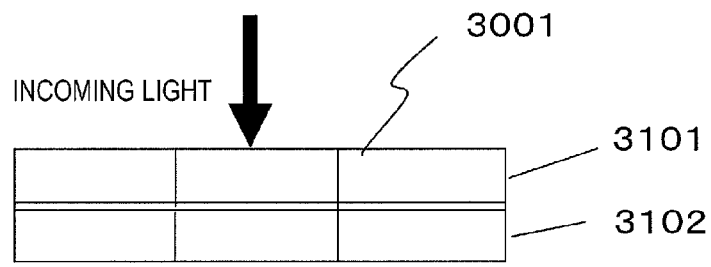
FIG. 4A is a cross-sectional view illustrating the configuration of an image sensor which may be used in the first embodiment of the present disclosure.
Figure 4B:
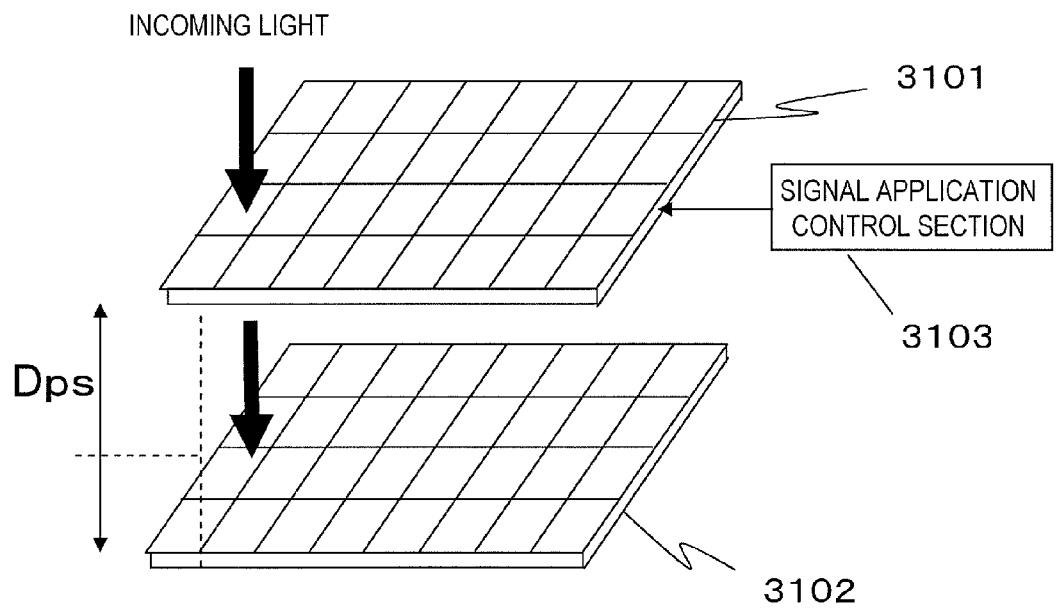
FIG. 4B is a perspective view illustrating the configuration of an image sensor which may be used in the first embodiment of the present disclosure.

FIGS. 4A and 4B are respectively a cross-sectional view and a perspective view illustrating the configuration of a main portion of the polarization image sensor 3001.

This polarization image sensor 3001 includes a plane of polarization changer 3101 which is located closer to the light source and an intensity image sensor 3102 which receives the light that has been transmitted through the plane of polarization changer 3101. The intensity image sensor 3102 is an image sensor (such as a CCD or MOS sensor) which obtains intensity information by capturing an image. In this polarization image sensor 3001, one pixel of the intensity image sensor 3102 corresponds to one pixel of the plane of polarization changer 3101 unlike the known pattern polarizer mosaic polarization image sensor. More specifically, the plane of polarization changer 3101 includes a liquid crystal layer and two electrodes that sandwich the liquid crystal layer between them, and can control the optical property of the liquid crystal layer upon the application of a voltage to the electrodes. In such a plane of polarization changer 3101, each pixel may be set to transmit plane polarized light, which is polarized in an arbitrary direction, independently of the other pixels. However, the plane of polarization changer 3101 of this embodiment operates so that every pixel has a polarized light transmission plane in the same direction. As will be described in detail later, the plane of polarization changer 3101 can work so as to sequentially change the polarization directions of light rays to be incident on respective pixels of the intensity image sensor. Thus, according to this embodiment, in calculating the polarization information, there is no need to perform any spatial image processing operation using surrounding pixel values. As a result, the resolution of the polarization image can maintain the resolution of the intensity image sensor 3102.

In response to a signal that may or may not be applied from a signal application control section 3103, the plane of polarization changer 3101 can quickly change the polarized light transmission directions into any of the four directions (such as the ones defined by 0, 45, 90 and 135 degrees) with time. As a result, the polarization image sensor 3001 of this embodiment can obtain the degree of polarization and the angle of polarization on a pixel-by-pixel basis.

In this embodiment, the distance Dps between the plane of polarization changer 3101 and the intensity image sensor 3102 is substantially equal to zero. That is why if the polarized light transmission axis of the polarizer that is located right in front of each pixel has changed into three or more directions, no pixel positions shift between the polarizer and the image sensor and good polarization information can be obtained. As a result, a fine super-resolution function can be used effectively within a single pixel.

Figure 5A:
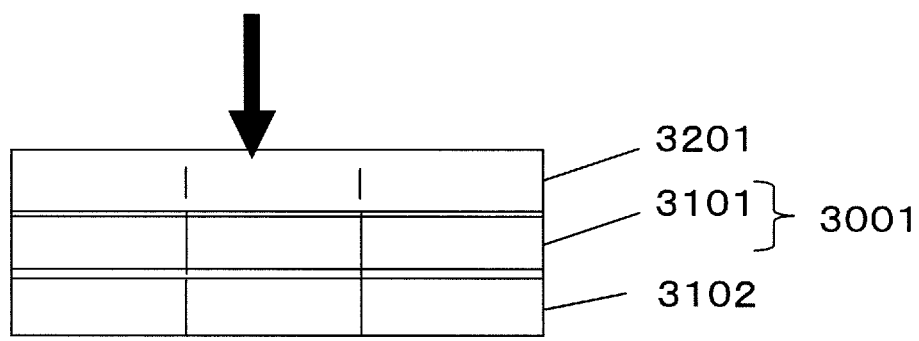
FIG. 5A is a cross-sectional view illustrating the configuration of another image sensor which may be used in the first embodiment of the present disclosure.
Figure 5B:
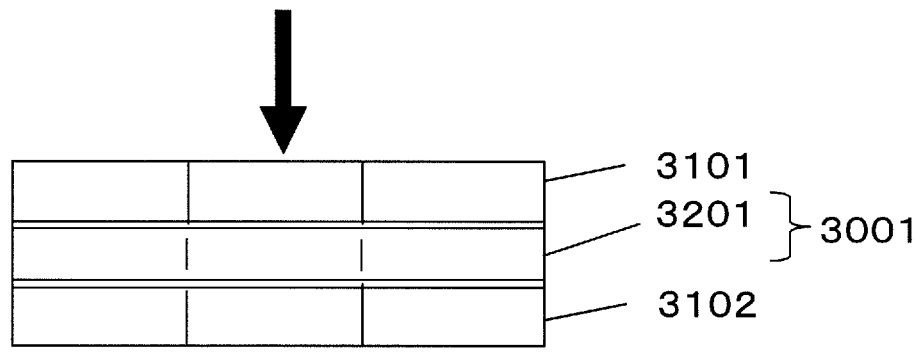
FIG. 5B is a cross-sectional view illustrating the configuration of still another image sensor which may be used in the first embodiment of the present disclosure.

FIGS. 5A and 5B illustrate other configurations for the polarization image sensor 3001. With this configuration, a color image and a polarization image can be captured at the same time on a pixel-by-pixel basis. In the configuration shown in FIG. 5A, incoming light passes through color filters 3201 first and the plane of polarization changer 3101 next, and then reaches the intensity image sensor 3102. On the other hand, in the configuration shown in FIG. 5B, incoming light passes through the plane of polarization changer 3101 first and the color filters 3201 next, and then reaches the intensity image sensor 3102.

Figure 6:
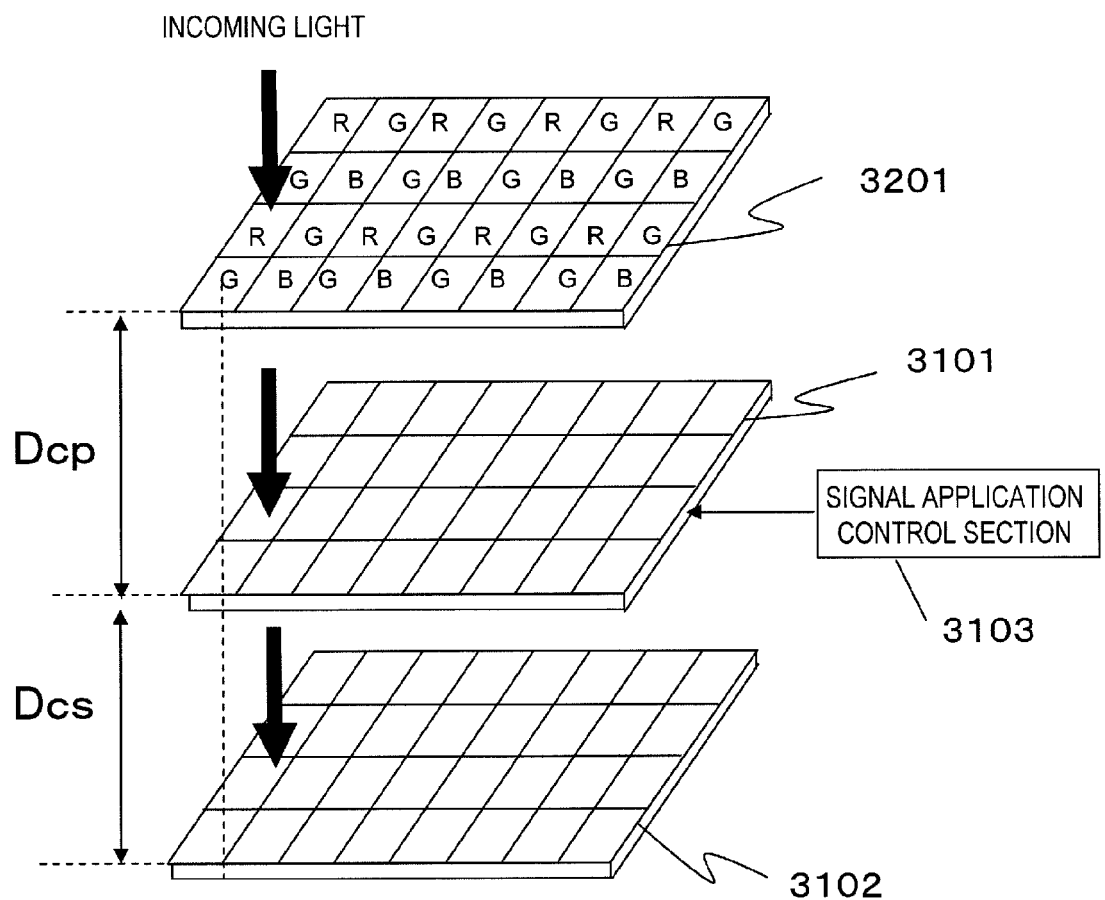
FIG. 6 is a perspective view illustrating a polarization image sensor with color filters.

FIG. 6 is a perspective view illustrating the configuration shown in FIG. 5A in further detail. The distance Dcp between the color filters 3201 and the plane of polarization changer 3101 and the distance Dcs between the plane of polarization changer 3101 and the intensity image sensor 3102 are both substantially equal to zero.

Figure 7:
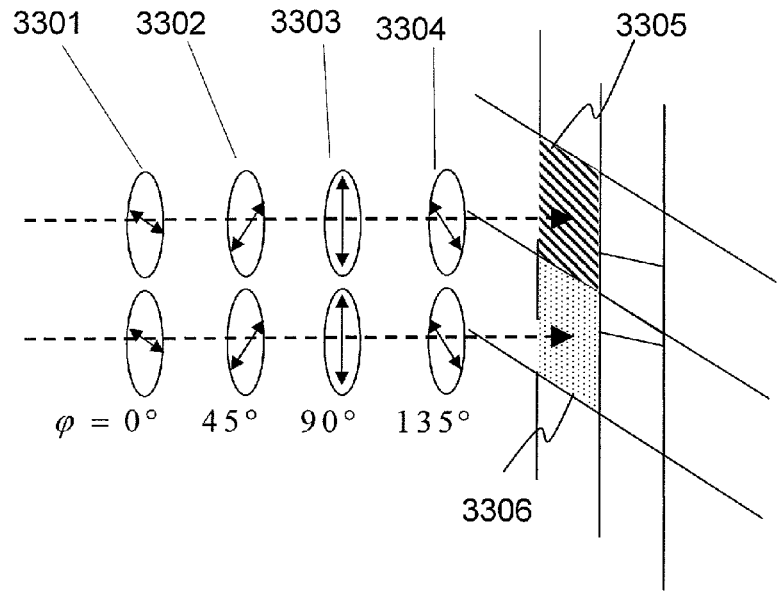
FIG. 7 illustrates how the polarization image sensor operates with time.
Figure 8A:
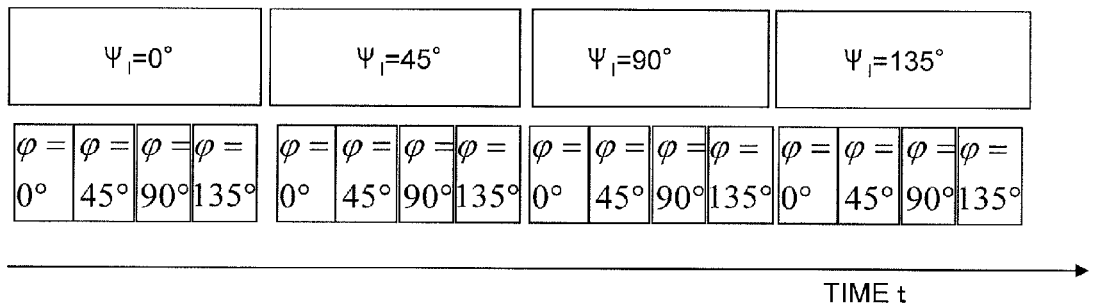
FIG. 8A shows a series of timings to control the rotation of a plane of polarization of the illuminating light and the rotation of a plane of polarization for image capturing temporally.

FIGS. 7 and 8A illustrate how this polarization image sensor operates. FIG. 7 shows that polarized light intensities about four directions with mutually different $\phi$ can be obtained for each pixel of the image sensor. Specifically, while the light that is going to be incident on a pixel 3305 of the intensity image sensor 3102 is transmitted through its corresponding pixel of the plane of polarization changer 3101, the polarization state of that light changes from the state 3301 into the states 3302, 3303 and 3304. That is to say, at the corresponding pixel of the plane of polarization changer 3101, the plane of the transmitted polarized light rotates to have four different direction $\phi$ of 0, 45, 90 and 135 degrees. Consequently, the polarized light intensities in the respective directions are observed temporally sequentially. In another pixel 3306, polarized light intensities are separately observed in four directions. Although the pixels 3305 and 3306 may have two independent sets of observation angles, the plane of the transmitted polarized light is supposed in this example to rotate in the same phase at every pixel.

FIG. 8A shows the timings when the synchronizer 112 shown in FIG. 1C makes the polarization image sensor operate temporally synchronously with the illuminating light, of which the plane of polarization is rotated by the plane of polarization control element 106. In FIG. 8A, the abscissa indicates the passage of time. In the example illustrated in FIG. 8A, first of all, when the plane of polarization of the illumination has an angle ψI of 0 degrees, images are captured with the plane of polarization of the polarization image sensor 3001 rotated at high speeds to define the angles $\phi$ of 0, 45, 90 and 135 degrees in this order. Next, when the plane of polarization of the illumination rotates to an angle ψI of 45 degrees, the polarization image sensor 3001 performs the same operation once again. And then by performing the same operation repeatedly when ψI=90 degrees and when ψI=135 degrees, sixteen images are captured in total to end one set of sequences. Supposing the time it takes to capture a single image by irradiating the object with illumination with single ψI and observing at a single angle of observation $\phi$ is T, it takes a time of 16T to end one set of sequences. For that reason, it is recommended that a high sensitivity image sensor that can capture images at high rates be selected as the polarization image sensor 3001 and that the illumination have sufficiently high illuminance.

Figure 8B:
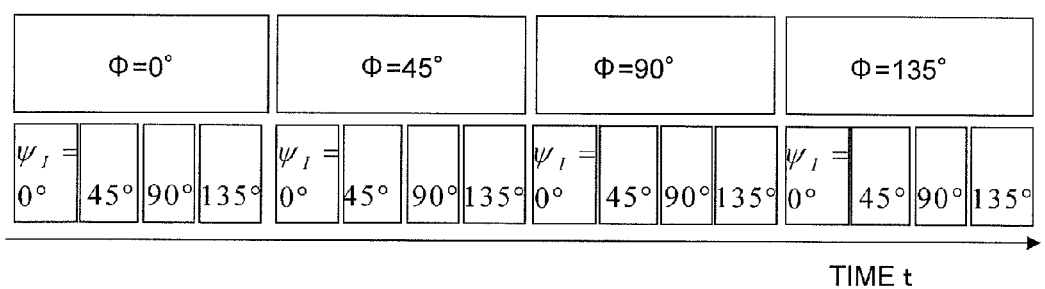
FIG. 8B shows another series of timings to control the rotation of a plane of polarization of the illuminating light and the rotation of a plane of polarization for image capturing temporally.

The polarization images do not have to be captured following the pattern shown in FIG. 8A. Alternatively, the timings to capture polarization images may also be controlled so that the plane of polarization of the illumination is rotated to every angle ψI with respect to single $\phi$ as in the example illustrated in FIG. 8B. Still alternatively, the control operation may also be carried out using a different timing chart in which these two patterns are combined together.

The variation in polarized light intensity as $\phi$ changes into four different values through the rotation is also subjected to fitting processing using a trigonometric function as in the variation in light intensity that has been described for the first embodiment. That processing will be described in detail later.

Next, it will be described how to estimate the distribution in a single pixel of the azimuth angles of a plurality of grooves that are present on the surface of the object 100 (i.e., super-resolution in a single pixel).

Figure 9:
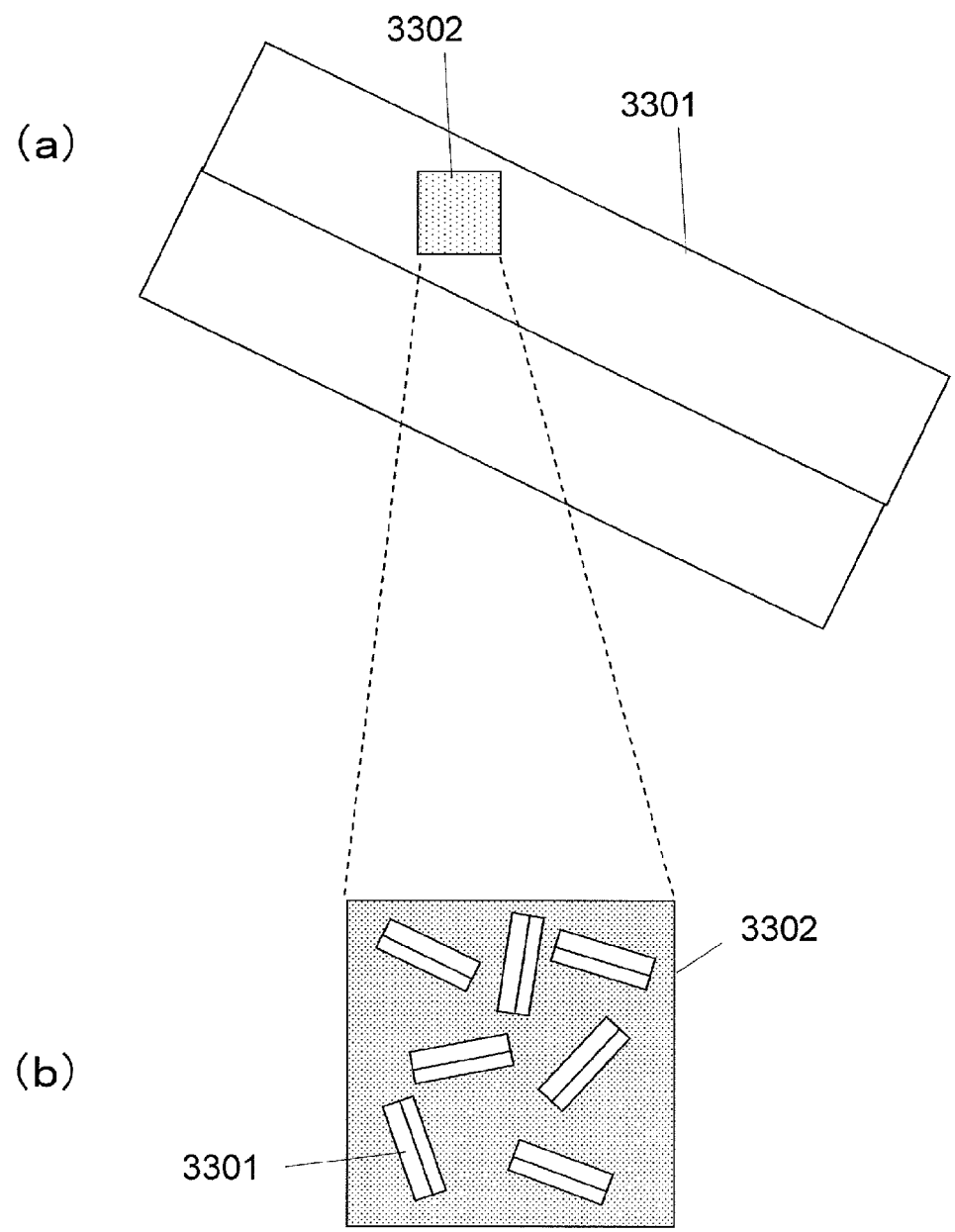
FIG. 9(a) illustrates a situation where a plurality of pixels are included in a single groove and FIG. 9(b) illustrates a situation where a plurality of grooves are included in a single pixel.

Portions (a) and (b) of FIG. 9 are top views respectively illustrating a relatively large groove on the object and a plurality of grooves that are smaller than a single pixel. In the object image shown in portion (a) of FIG. 9, the single groove 3301 is larger than the single pixel 3302. In the object image shown in portion (b) of FIG. 9, on the other hand, there are a lot of very small grooves in the single pixel. In that case, images of those grooves cannot be captured just by observing the light intensity on a pixel basis.

Figure 10:
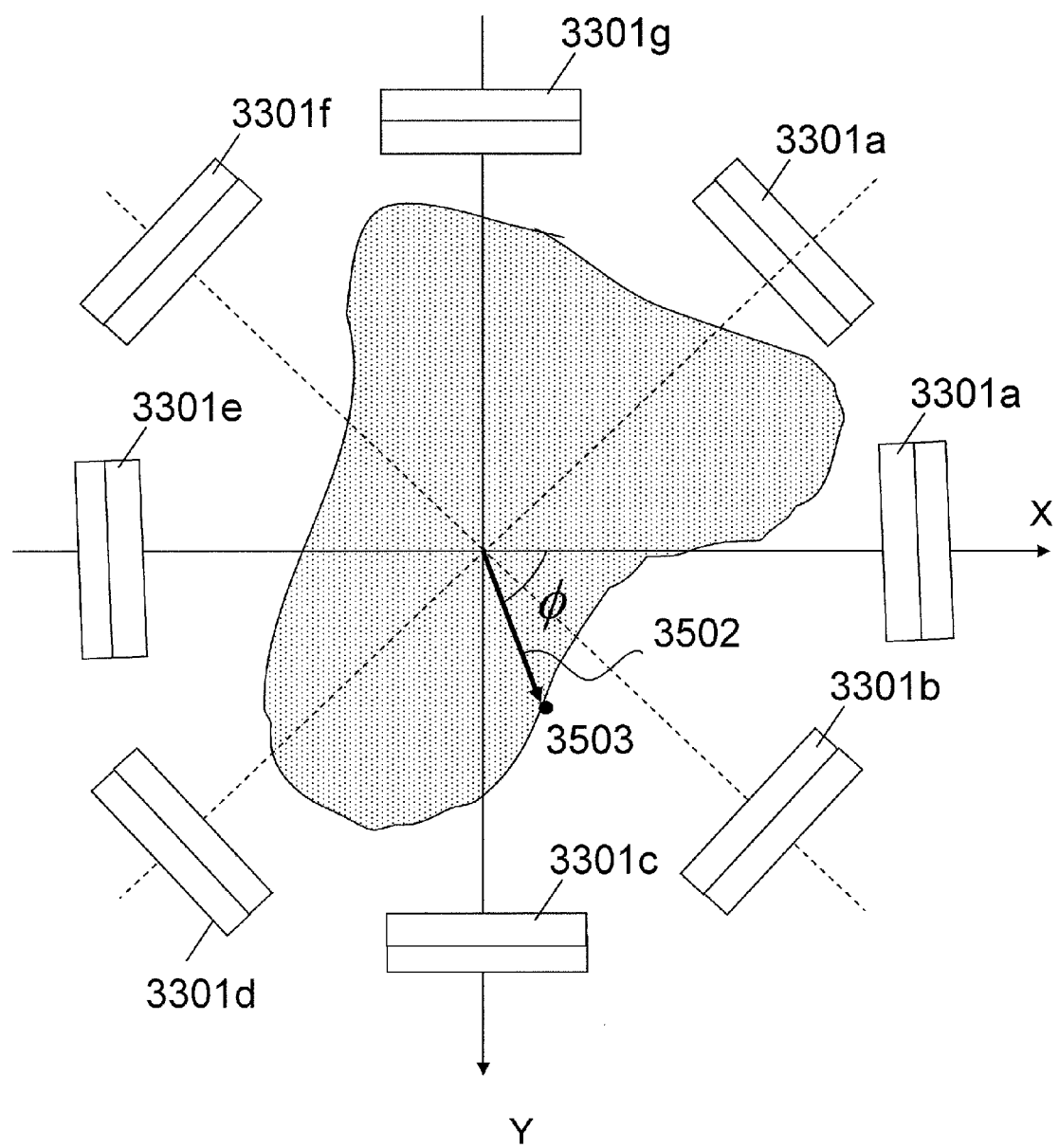
FIG. 10 Shows a function indicating the distribution of grooves in a single pixel.

FIG. 10 illustrates the distribution of grooves in a single pixel. The direction of each of those grooves is supposed to be defined by the angle ψ that indicates the direction that intersects with the principal axis of the groove at right angles. At the center of FIG. 10, shown is a distribution function D(ψ) represented by polar coordinates, of which the radial length is defined by the histogram frequency in the ψ direction. That is to say, as the function of the angle ψ indicated by the arrow 3502 shown in FIG. 10, the distance from the origin to the tip 3503 of the arrow 3502 is represented by D(ψ). The grooves 3301 included in a single pixel have random directions. And if it didn't depend on the angle ψ, the distribution function D(ψ) would draw a circle. The eight grooves 3301a, 3301b, ... and 3301h shown around the distribution function D(ψ) schematically illustrate grooves, of which the angle ψ are 0, 45, ... and 325 degrees, respectively.

To estimate the distribution function D(ψ) means estimating the distribution in a single pixel of the azimuth angles of grooves on the surface of an object.

The distribution function D(ψ) satisfies the following Equation (1):

$$\int_0^\pi D(\psi)d\psi = 1 \qquad (1)$$

When polarized light is observed, the fundamental period is 180 degrees, and therefore, the groove directions that can be estimated also have a period π. This distribution function can be subjected to a Fourier series expansion with respect to ψ in the following manner:

$$\begin{aligned} D(\psi) &= a_0 + \sum_{n=1} a_n\cos(n\psi) + b_n\sin(n\psi) \\ &= a_0 + a_1\cos(\psi) + b_1\sin(\psi) + a_2\cos(2\psi) + b_2\sin(2\psi) + \\ &\quad a_3\cos(3\psi) + b_3\sin(3\psi) + a_4\cos(4\psi) + b_4\sin(4\psi) + a_5\cos(5\psi) + \\ &\quad b_5\sin(5\psi) + L \end{aligned} \qquad (2)$$

where a0, a1, b1, a2, b2 and so on are coefficients. To determine the distribution function $D(\psi)$ these coefficients may be used.

Next, it will be described how the intensity varies when the plane of polarization of polarized light is rotated. In the following example, the object is not the mucosa of an organism's organ but an object made of a general material such as plastic or wood as an example. This example is taken because light is basically specular-reflected from the surface of the mucosa and because specular reflection from the surface of a dielectric material can be regarded as the same physical phenomenon irrespective of the material of the object.

Figure 11A:
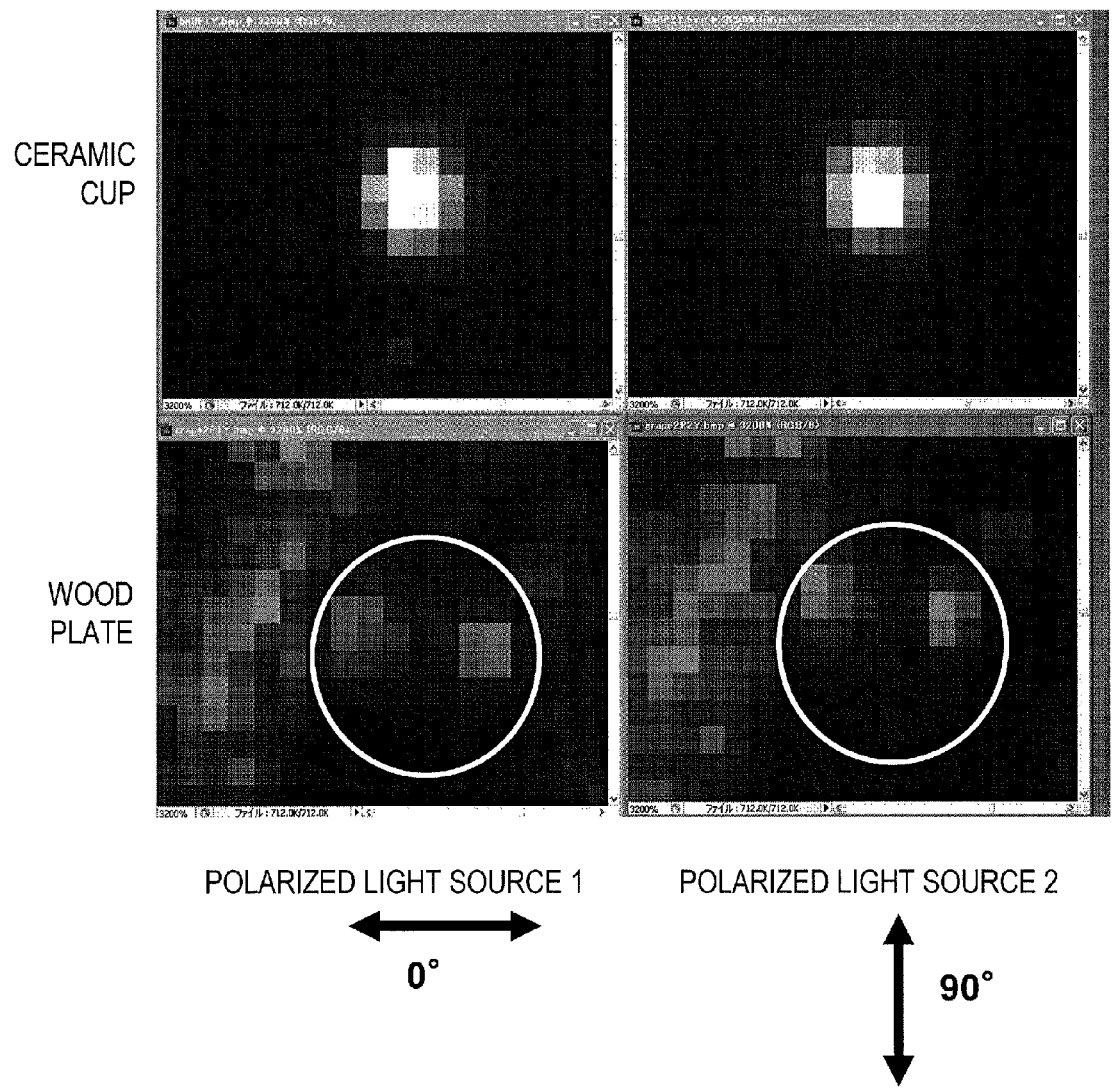
FIG. 11A Illustrates how intensity pattern images change as the polarization plane of a polarized light source rotates.
Figure 11B:
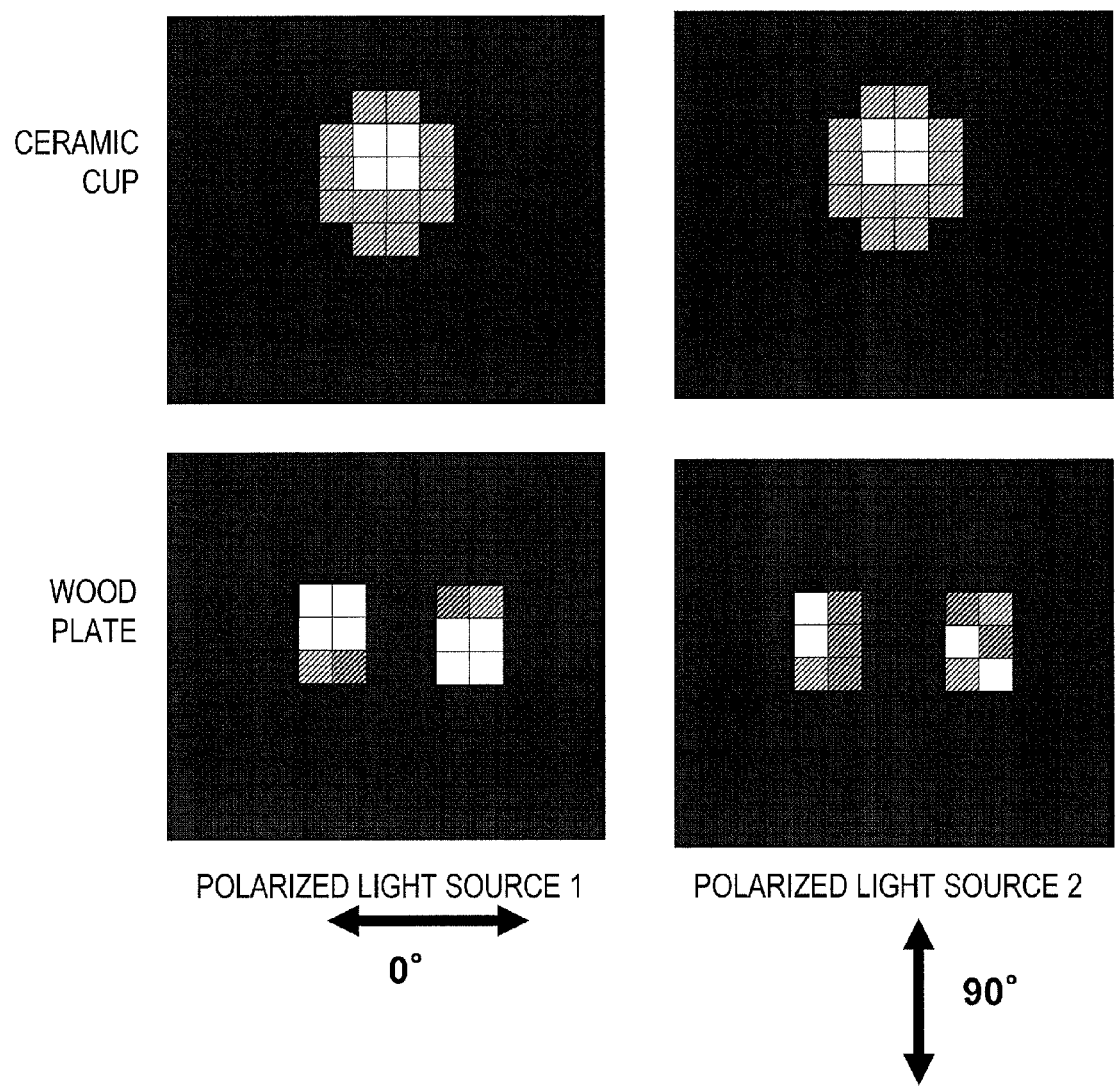
FIG. 11B schematic representations illustrating how intensity pattern images change as the polarization plane of a polarized light source rotates.

FIGS. 11A and 11B illustrate polarized images of a ceramic cup with a smooth surface and a wood plate with microfacet that were captured as objects by the present inventors. Specifically, the two images on the left-hand side of FIG. 11A are light intensity images that are obtained when the object is illuminated with polarized light with an incident plane of polarization angle $\psi I$ of 0 degrees. On the other hand, the two images on the right-hand-side of FIG. 11A are light intensity images that are obtained when the object is illuminated with polarized light with an incident plane of polarization angle $\psi I$ of 90 degrees.

Meanwhile, the four images shown in FIG. 11B are schematic representations of the four images shown in FIG. 11A. As can be easily from the images shown at the top of FIGS. 11A and 11B, even if the polarization plane of the polarized light was changed, no significant variation was observed in the intensity pattern of the ceramic cup with the smooth surface. As for the wood plate with a lot of micro-geometry, on the other hand, it turned out that when the angle $\psi I$ of the polarization plane of the polarized light was changed, a significant variation occurred in the light intensity image observed as can be seen easily from the images shown at the bottom of FIGS. 11A and 11B. Such a difference can be explained as follows.

Figure 12:
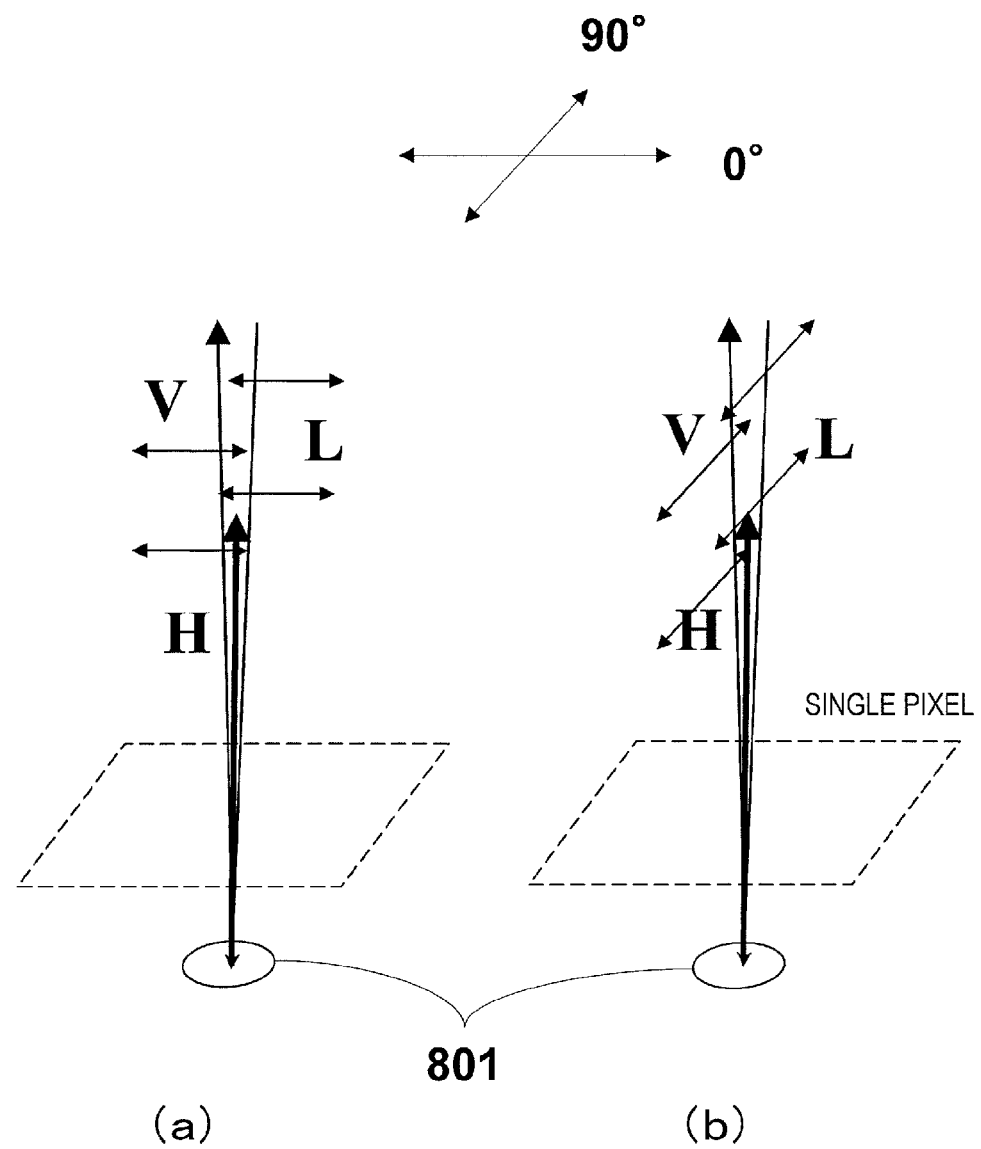
FIGS. 12(a) and 12(b) illustrate how incoming light that has come directly from over an object is incident on the object's surface and reflected once.
Figure 13:
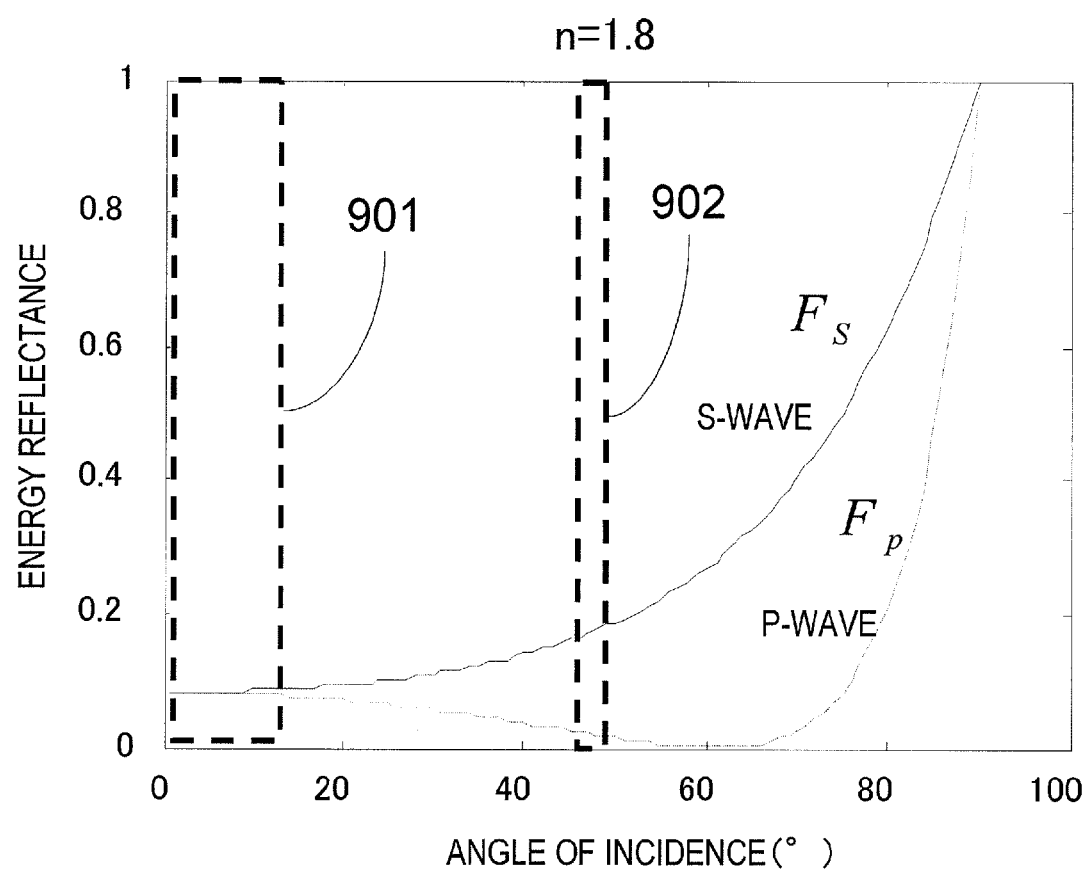
FIG. 13 is a graph showing how the Fresnel reflectances of P- and S-wave energies change with the angle of incidence (that is represented as the abscissa).

FIG. 12 illustrates how polarized light is incident on the surface 801 at an angle of incidence that is close to zero degrees and how the specular reflected light is observed with a camera. The respective angles defined by the polarization planes of the incident polarized light are different from each other by 90 degrees between portions (a) and (b) of FIG. 12. However, even though the reflected plane polarized light travels in a different direction from the incident light, the intensity (i.e., the energy) of the reflected light is almost the same as that of the incident light for the following reasons:

FIG. 13 is a graph showing the dependence of the specular reflectance according to the Fresnel theory on the angle of incidence. In FIG. 13, the abscissa represents the angle of incidence and the ordinate represents the Fresnel reflectance. These dependence curves are drawn on the supposition that the refractive index NN is 1.8. The angles of incidence of around 0 through around 15 degrees, which can be regarded as representing substantially perpendicular incidence, fall within the range 901. As can be seen from this graph, both P and S waves have substantially the same reflectance in this range 901. Therefore, if the polarized light is incident substantially perpendicularly onto the surface, then it makes almost no difference for the surface and the light is reflected in the same behavior, no matter whether the polarized light is actually a P-wave or an S-wave. This fact is satisfied extensively by any natural object with a refractive index n of 1.4 to 2.0.

As described above, if polarized light is incident on a smooth surface at an angle of incidence of almost zero degrees, reflected once and then observed, the energy of the reflected light does not change, and the intensity Y observed does not change, either, even when the plane of polarization of the polarized light is rotated by $\psi I$ degrees.

Figure 14A:
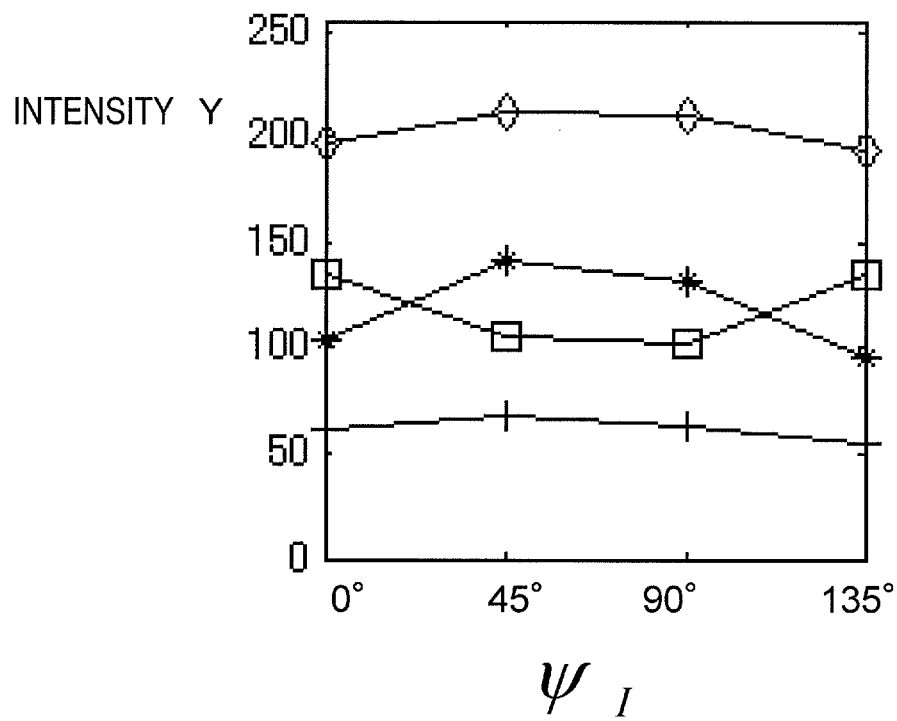
FIG. 14A is a graph showing how the intensity value of a pixel varies as the plane of polarization of polarized light is rotated.
Figure 14B:
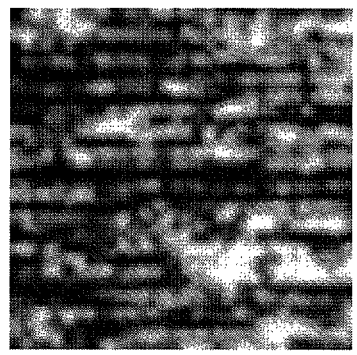
FIG. 14B is a photograph showing the surface shape of a sample that was used to get the data shown in the graph of FIG. 14A.
Figure 14C:
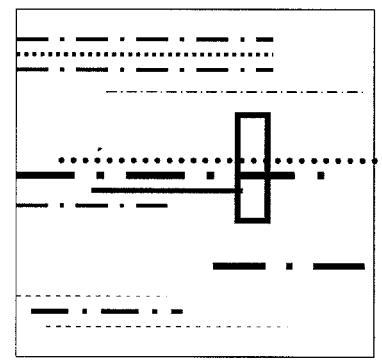
FIG. 14C schematically illustrates the surface shape shown in FIG. 14B.

FIG. 14A is a graph showing how the intensity value of the same pixel varied in a situation where a light intensity image was shot with the plane of polarization of the polarized light, impinging on the surface of a wood plate, changed. FIG. 14B is a light intensity image of that wood plate as the object of shooting (i.e., a light intensity image under non-polarized light). And FIG. 14C schematically illustrates the surface micro-geometry of the wood plate shown in FIG. 14B.

Figure 15:
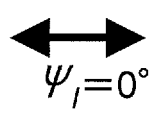
FIG. 15(a) shows the polarization directions of polarized light sources and FIG. 15(b) shows how the light intensity varies according to the polarized light source.
Figure 15:
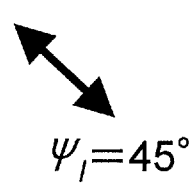
Figure 15:
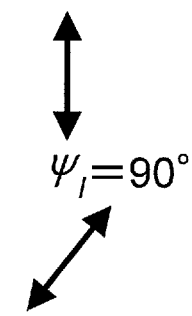
Figure 15:
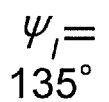
Figure 15:
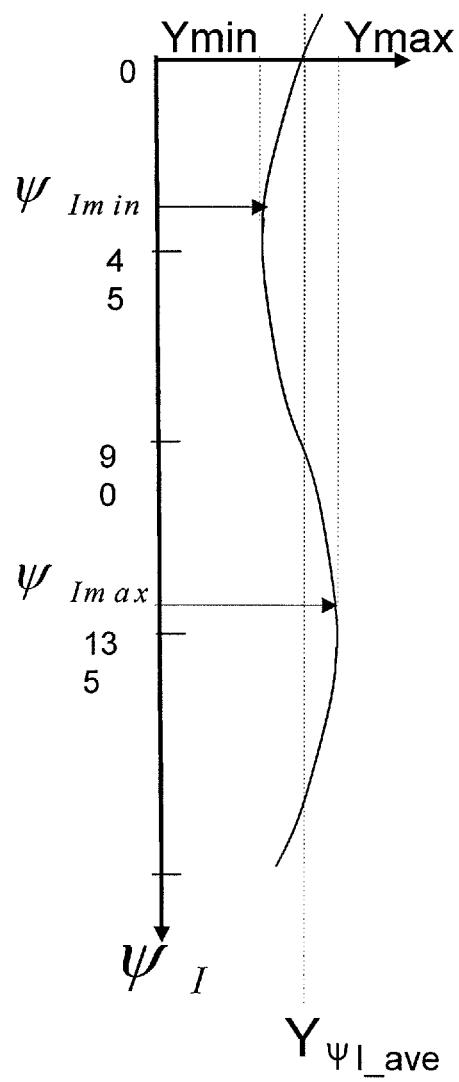

FIG. 15 shows the behavior of the intensities Y of a particular pixel of a light intensity image that were obtained when the plane of polarization of the polarized light had angles $\psi I$ of 0, 45, 90 and 135 degrees, respectively. As can be seen from this graph, the intensity Y varied periodically according to the angle $\psi I$ of the plane of polarization of each polarized light. The surface of the wood plate is not smooth but has a lot of grooves, where the incident light produces interreflection. Consequently, the intensity Y would vary according to the angle $\psi I$ of polarization of the light. The reason will be described in detail below.

Figure 16:
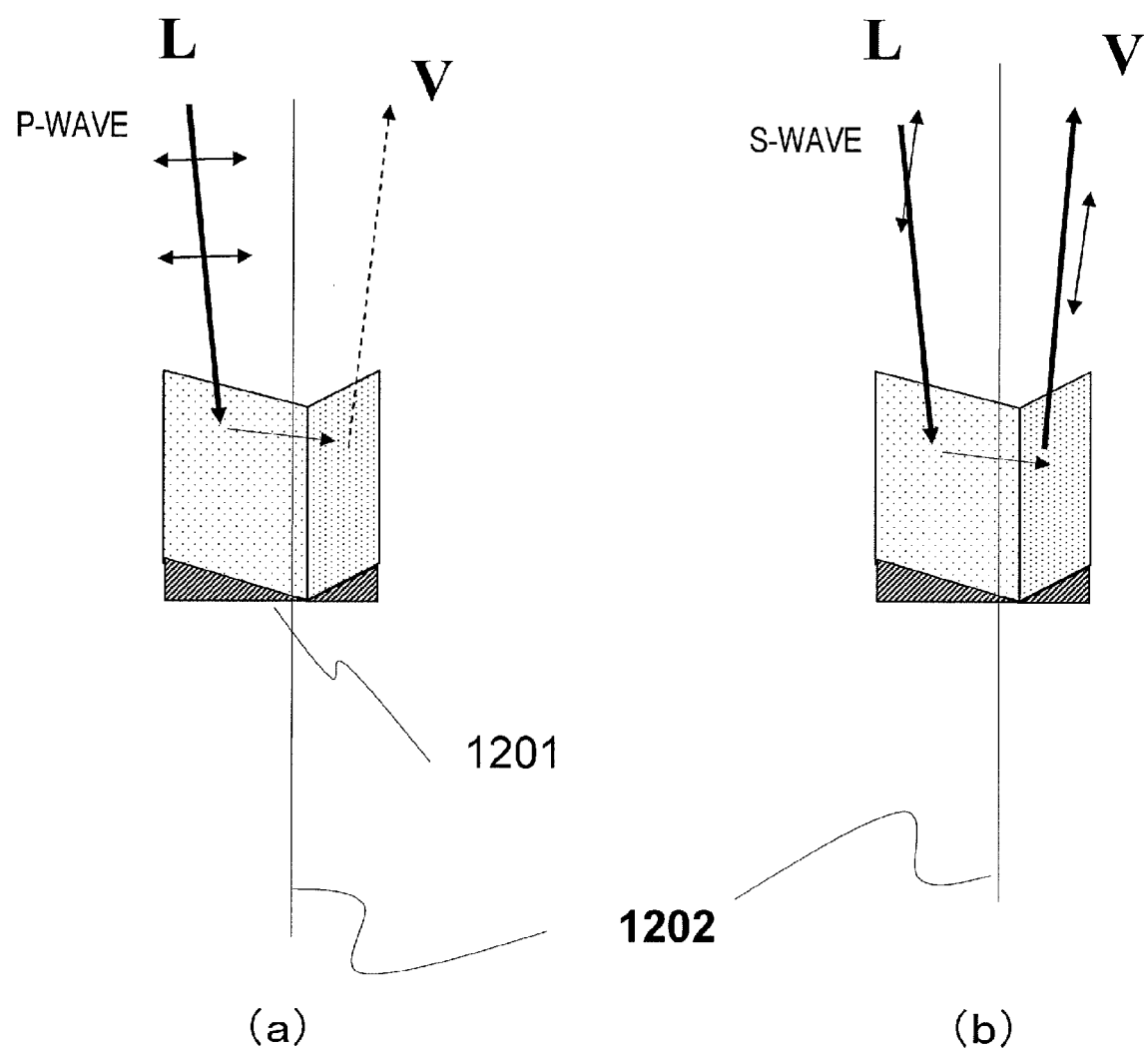
FIGS. 16(a) and 16(b) illustrate how the intensity of polarized reflected light varies due to interreflection.

FIG. 16 illustrates how a groove 1201 that has been formed on a surface produces interreflection twice on its slopes. That kind of interreflection would be produced on an uneven surface of various natural objects including cloth, wood, human skin and leather. In this case, the properties of reflections are important the first and second times around, but the interreflection is almost negligible for the third time and on, because the intensity is small. Thus, in this example, only a situation where the interreflection occurs twice will be described. Generally speaking, if the properties of reflection are roughly classified into specular reflection and diffuse reflection, there should arise one of the following four situations:

1) diffuse reflection the $1^{st}$ time around and specular reflection the $2^{nd}$ time around;
2) diffuse reflection both of the $1^{st}$ and $2^{nd}$ times around;
3) specular reflection the $1^{st}$ time around and diffuse reflection the $2^{nd}$ time around; and
4) specular reflection both of the $1^{st}$ and $2^{nd}$ times around.

Among these four situations, in situations 1) and 2), when the light is diffuse-reflected the first time around, the diffuse-reflected light gets non-polarized and is reflected in every direction. However, the results of experiments revealed that when the object was colored and had low intensity, the diffuse reflection component of this first time around was a minor one, which means that a relatively small quantity of light penetrated the object. Rather, the specular reflection in situations 3) and 4), which is complementary to situation 1), should prevail over the diffuse reflection according to Fresnel theory. Meanwhile, if diffuse reflection is produced the second time around as in situation 3), it can be seen easily, considering the geometric relation between the incident and reflected light rays, that situation 3) involves situation 4). In that case, no matter whether the degree of polarization or intensity is used as a reference, the major intensity component will be produced by specular reflection.

Consequently, situation 4), in which specular reflection is produced both of the first and second times around, may be regarded as the dominant phenomenon. If the tilted surface in the groove is not quite smooth and if the illumination is not quite parallel light, even specular reflected light is not ideal one. That is why the present inventors confirmed via experiments that even if the specular reflection condition was not satisfied completely, these two reflections could be observed, and the image could be captured, relatively easily and the polarization property was caused by the specular reflection.

Next, look at portions (a) and (b) of FIG. 16, in which illustrated is a portion of a groove 1201 on the surface of an object. On the object's surface, at least a portion of the groove 1201 runs in one direction, which will be referred to herein as the "principal axis direction". Actually, however, the groove 1201 does not have to run linearly but may be a curved one, too. Even in such a curved groove, its portion can also be approximated to be a linear groove that runs in the principal axis direction.

It should be noted that a cross section of the groove 1201 on the object's surface can be approximated to be a V-shape. That is why a groove on the surface of an organism's organ can be called a "V-groove". However, a cross section of such a V-groove does not have to have an exactly V-shape but may have a curved portion, too. In any case, as long as there is a groove with a generally "V-shaped" cross section on the object's surface and as long as there arises a phenomenon that the illumination light is twice reflected from the surface and returns, the following description is applicable.

As shown in portion (a) of FIG. 16, polarized light incident perpendicularly to the principal axis direction 1202 of the groove is a P-wave. Look at FIG. 13 again, and it can be seen that if the object's groove 1201 has a tilt angle of approximately 45 degrees and if light is incident from right over the groove 1201, the reflectance of a P-wave becomes much lower than that of an S-wave in the range 902 of that angle of incidence as can be seen from the graph showing the Fresnel reflectance. The reflectance of the P-wave further decreases as the P-wave goes through reflection first and second times around. On the other hand, the S-polarized light shown in portion (b) of FIG. 16 does not have its reflectance decreased so much even after having gone through the reflections first and second times around. As a result, on the plane of polarization of the P-wave that has been incident on the groove, the reflected light comes to have very low energy and decreased intensity. On the other hand, on the incident plane of polarization of the S-wave, the reflected light has not had its energy attenuated so much and still maintains high intensity.

If the surface groove is supposed to be as such, the variation in the intensity of the reflected light that was caused by rotating the plane of polarization of the incident light in an experiment can be accounted for.

The present inventors discovered that the function representing the variation in intensity Y that was caused by getting the polarized light reflected twice from the groove changed in substantially the same way as in a situation where non-polarized light was incident there. Hereinafter, this respect will be described.

Figure 17:
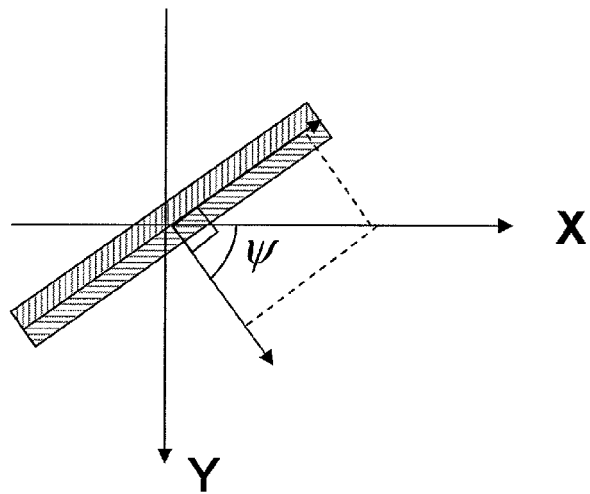
FIGS. 17(a), 17(b) and 17(c) illustrate a groove on the object's surface as viewed from right over that surface.
Figure 17:
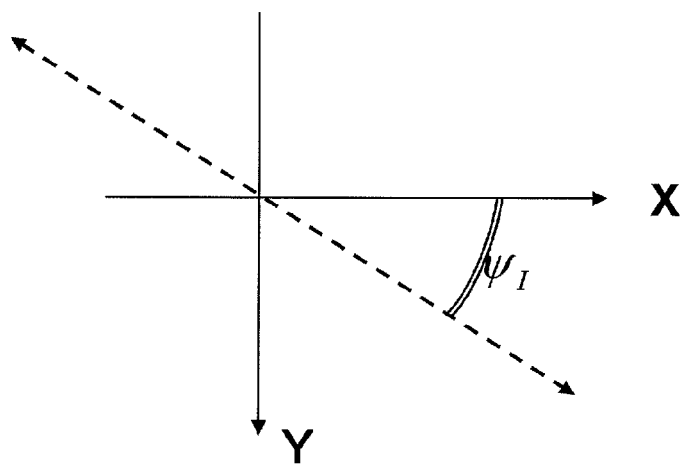
Figure 17:
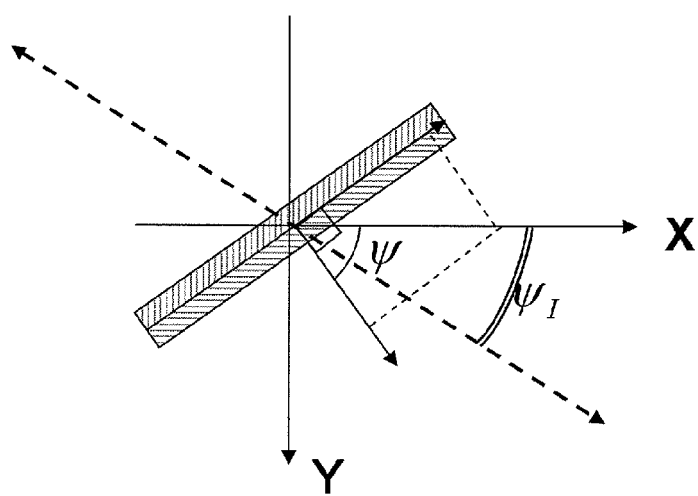

FIG. 17(a) illustrates a groove on the object's surface as viewed from right over that surface, which corresponds to looking down on FIG. 16 from right over the paper. In FIG. 17(a), shown are X and Y coordinates on a plane that is parallel to the image capturing plane. Also shown is the angle ψ formed between the direction that intersects at right angles with the principal axis direction 1202 of the groove 1201 and the positive X-axis direction. FIG. 17(b) shows the angle ψI of the plane of polarization of the polarized light that has been incident on the object. And FIG. 17(c) illustrates, in combination, what is illustrated in FIGS. 17(a) and 17(b) in the same drawing. In the following description, the direction of the groove will be specified herein by the angle ψ, which is different from the azimuth angle of the groove's principal axis by 90 degrees.

Figure 18A:
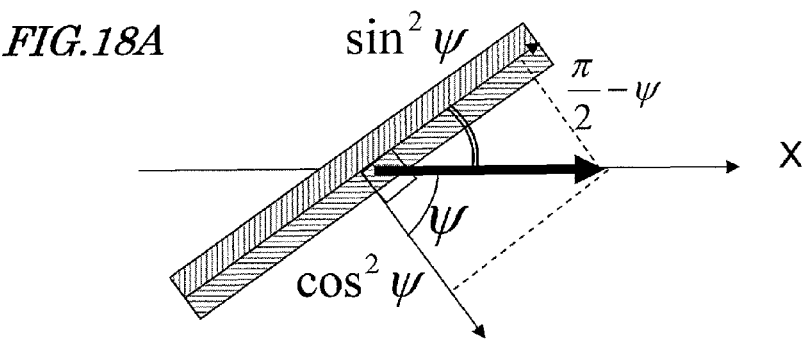
FIG. 18A illustrates a situation where polarized light is incident on a groove at ψI=0 degrees.
Figure 18B:
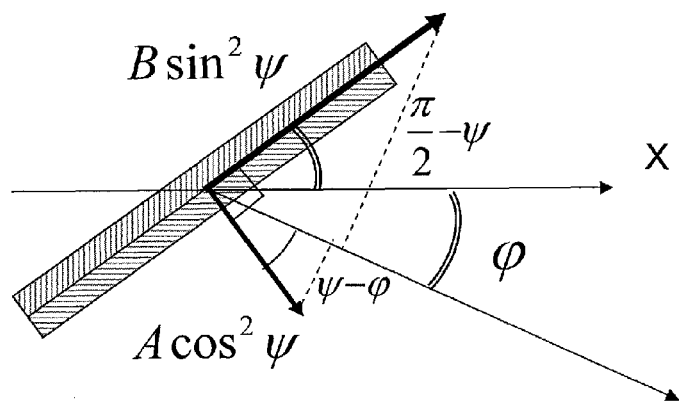
FIG. 18B illustrates a situation where reflected light is produced parallel and perpendicularly to the azimuth angle ψ of the groove in the state shown in FIG. 18A.

FIG. 18A illustrates the energies of incident light to be distributed perpendicularly and horizontally with respect to a groove in a situation where the plane of polarization is supposed to be aligned with the X-axis for the sake of simplicity (i.e., ψI=0). The direction of the groove is specified by the angle ψ. Suppose the incident light is reflected twice in the groove as shown in FIG. 16. In that case, the intensity of plane polarized light, of which the plane of polarization has a certain angle φ, is measured. FIG. 18B shows the angle ψ of the plane polarized light, of which the intensity is measured. If the polarized light intensity at the angle φ is represented by I (ψ, φ), then the intensity can be represented by the following Equation (3) where the energy reflectances in the groove direction (ψ) and the principal axis direction (π/2−ψ) are identified by A and B, respectively:

$$I(\psi,\phi) = A \cos^2 \psi \cos^2(\psi-\phi) + B \sin^2 \psi \sin^2(\psi-\phi) \qquad (3)$$

By modifying Equation (3), this polarized light intensity I (ψ, φ) can be represented by the following Equation (4):

$$I(\psi, \varphi) = \frac{(A+B)}{4} + \qquad (4)$$

$$\frac{(A-B)}{4}\cos 2\psi + \left[\frac{(A+B)}{8} + \frac{(A-B)}{4}\cos 2\psi + \frac{(A+B)}{8}\cos 4\psi\right]$$

$$\cos 2\varphi + \left[\frac{(A-B)}{4}\sin 2\psi + \frac{(A+B)}{8}\sin 4\psi\right]\sin 2\varphi$$

As can be seen from this Equation (4), the polarized light intensity I (ψ, φ) varies in the period π with respect to φ.

Suppose the incident plane of polarization angle is the general value ψI instead of 0 degrees. In that case, it can be seen, from the foregoing discussion, that the polarized light intensity in a situation where the incident plane of polarization angle is ψI and the viewing angle is φ is given by the following Equation (5):

$$I(\psi-\psi_I, \varphi-\psi_I) = \frac{(A+B)}{4} + \frac{(A-B)}{4}\cos 2(\psi-\psi_I) + \qquad (5)$$

$$= \left[\frac{(A+B)}{8} + \frac{(A-B)}{4}\cos 2(\psi-\psi_I) + \frac{(A+B)}{8}\cos 4(\psi-\psi_I)\right]$$

$$\cos 2(\varphi-\psi_I) + \left[\frac{(A-B)}{4}\sin 2(\psi-\psi_I) + \frac{(A+B)}{8}\sin 4(\psi-\psi_I)\right]$$

$$\sin 2(\varphi-\psi_I)$$

The polarized light intensity given by this Equation (5) is measured at a viewing angle φ in a particular direction. That is why in measuring the average intensity of non-polarized light, the polarized light intensity represented by Equation (3) needs to be integrated for one period with respect to the viewing angle φ. In this case, one period is 180 degrees=π. As a result of this integral operation, the sine and cosine function with respect to φ become equal to zero. That is to say, the light intensity PY (ψI, ψ) to be measured in a situation where polarized light with an incident plane of polarization angle ψI is incident on a groove that is specified by an angle ψ and then reflected twice can be represented as a periodic function of 180 degrees with respect to ψI as in the following Equation (6):

$$PY(\psi_I, \psi) = \int_0^\pi I(\psi - \psi_I, \varphi - \psi_I) d\varphi \quad (6)$$
$$= \frac{A+B}{4} + \frac{A-B}{4}\cos 2(\psi - \psi_I)$$

If the light intensity PY (ψI, ψ) becomes a cosine function of ψI as represented by this Equation (6), the light intensity PY (ψI, ψ) comes to have a maximum value when ψ=ψI. That is why such an angle ψ=ψI at which the light intensity PY (ψI, ψ) has a maximum value will be referred to herein as an "intensity maximizing angle YPH". As for the amplitude of variation, considering that the cosine function term varies within the range of +1 through −, the degree of modulation of the intensity variation can be considered. And that ratio will be referred to herein as a "degree of light intensity modulation YD", which can be calculated by the following Equation (7):

$$YD = \frac{MAX - MIN}{MAX + MIN} = \frac{B-A}{A+B} \quad (7)$$

It should be noted that the intensity maximizing angle YPH and the degree of intensity modulation YD are given on a pixel-by-pixel basis. That is why an image, in which the intensity maximizing angle YPH is set for each of the constituent pixels thereof, will be referred to herein as an "intensity maximizing angle image YPH". Likewise, an image, in which the degree of intensity modulation YD is set for each of the constituent pixels thereof, will be referred to herein as a "degree of intensity modulation image YD".

In this case, the intensity maximizing angle YPH and the degree of intensity modulation YD are quantities corresponding to a polarized light principal axis angle and a degree of polarization, respectively, in normal polarized light measuring. However, their quantitative relation has not been defined clearly yet. Thus, in order to clarify their relation, let us consider what polarization state twice-reflected light will have in a situation where non-polarized light has been incident on a groove.

Figure 19:
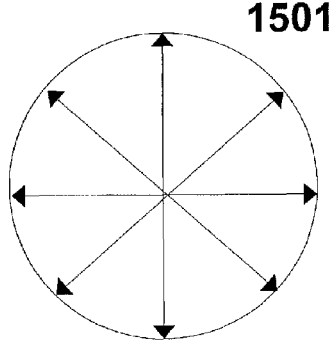
FIG. 19 illustrates a situation where non-polarized light is incident on a groove and reflected light is produced parallel and perpendicularly to the azimuth angle ψ of the groove.
Figure 19:
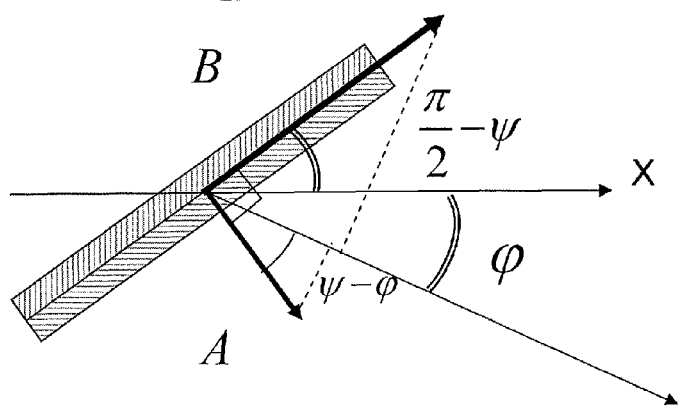

FIG. 19 illustrates a situation where non-polarized light 1501 has been incident on a groove. If the non-polarized light 1501 has been incident on a groove that has an angle ψ, then its energy would be equally distributed to the principal axis direction of the groove and the direction that intersects with the former direction at right angles. That is why energies multiplied by their energy reflectances A and B would be emitted in that groove's principal axis direction and the direction that intersects with the principal axis direction at right angles, respectively. If the polarized light is measured at an angle φ, the polarized light intensity will have its maximum value (at the reflectance B) in the groove's principal axis direction and have its minimum value (at the reflectance A) in that direction that intersects with the principal axis direction at right angles as already described with reference to FIG. 16. The degree of polarization DOP is calculated by the following Equation (8):

$$DOP = \frac{MAX - MIN}{MAX + MIN} = \frac{B-A}{A+B} \quad (8)$$

As can be seen from the foregoing discussion, it turned out that the intensity maximizing angle YPH, which is the phase angle of the light intensity variation in a situation where the angle ψI of the plane of polarization of polarized light has been rotated, agrees with the polarized light principal axis when non-polarized light is radiated. Likewise, it also turned out that the degree of intensity modulation YD, which is the amplitude of the light intensity variation in a situation where the angle ψI of the plane of polarization of polarized light has been rotated, agrees with the degree of polarization DOP when non-polarized light is radiated. Consequently, the Fresnel reflection theory and the surface normal discussion on the supposition that non-polarized light is radiated can be used to analyze a variation in polarized light intensity according to the present disclosure.

The image processing processor 3002 of this embodiment gets the intensity maximizing angle image YPH and the degree of intensity modulation image YD as described above, thereby obtaining information about the object's surface micro-geometry.

The polarized light intensity in a particular direction φ in a situation where polarized light ψI has been incident on one groove, of which the direction is defined by an angle ψ, is given by the following Equation (5). To calculate the intensity observed from a set of grooves with the distribution represented by Equation (1), double integration is performed in the grooves' direction and in the observation direction:

$$P\_Y(\psi_I) = \int_0^\pi d\psi \int_0^\pi d\varphi D(\psi) I(\psi - \psi_I, \varphi - \psi_I) \quad (9)$$

If integration is performed by substituting Equations (1) and (5) into Equation (9), then not only every odd number of times frequency term but also 4× or more even number of times frequency term of the Fourier series will disappear. As a result, the result of the double integration represented by Equation (9) becomes as follows:

$$P\_Y(\psi_I) = \int_0^\pi d\theta \left[ \frac{A+B}{4} + \frac{A-B}{4}\cos 2(\psi - \psi_I) \right] \left[ \begin{array}{c} a_0 + a_2\cos 2\psi + \\ b_2\sin 2\psi \end{array} \right] \quad (10)$$
$$= \pi^2\left(\frac{A+B}{4}\right)a_0 + \pi^2\left(\frac{A-B}{8}\right)a_2\cos 2\psi_I + \pi^2\left(\frac{A-B}{8}\right)b_2\sin 2\psi_I$$
$$= \pi^2\left(\frac{A+B}{4}\right)a_0 + \pi^2\left(\frac{A-B}{8}\right)\sqrt{a_2^2 + b_2^2}\cos 2(\psi_I - \psi_0)$$

The conclusion that can be derived here is that if the intensity variation is observed with ψI changed three times, a0, a2 and b2, which are the expansion coefficients of the groove distribution function, can be estimated.

According to this embodiment, what is obtained when the plane of polarization angle ψI of the illumination is changed is not only the intensity variation but also the intensity of polarized light in a certain observation direction φ to be observed by the polarization image sensor on a pixel-by-pixel basis. As a result, more information can be obtained about the expansion coefficient of the distribution function. As described above, the polarized light intensity in a particular direction φ in a situation where polarized light ψI has been incident on one groove, of which the direction is defined by an angle ψ, is given by Equation (5). Consequently, to calculate the polarized light intensity observed from a set of grooves with the distribution represented by Equation (1), integration needs to be performed in the grooves' direction:

$$P\_P(\psi_I, \varphi) = \int_0^\pi D(\psi)I(\psi - \psi_I, \varphi - \psi_I)d\psi \quad (11)$$

If calculation is made with Equations (5) and (1) substituted into this Equation (11), then $$P\_P(\psi_I, \varphi) = \pi a_0 \frac{A+B}{4} + a_2 \frac{\pi(A-B)}{8}\cos2\psi_I + b_2\frac{\pi(A-B)}{8}\sin2\psi_I + \quad (12)$$

$$\left[a_0\frac{\pi(A+B)}{8} + a_2\frac{\pi(A-B)}{8}\cos2\psi_I + \right.$$
$$\left. b_2\frac{\pi(A-B)}{8}\sin2\psi_I + a_4\frac{\pi(A+B)}{16}\cos4\psi_I + \right.$$
$$\left. b_4\frac{\pi(A+B)}{16}\sin4\psi_I\right]$$

$$\cos2(\varphi-\psi_I) + \left[-a_2\frac{\pi(A-B)}{8}\sin2\psi_I + \right.$$
$$\left. b_2\frac{\pi(A-B)}{8}\cos2\psi_I - \right.$$
$$\left. a_4\frac{\pi(A+B)}{16}\sin4\psi_I + \right.$$
$$\left. b_4\frac{\pi(A+B)}{16}\cos4\psi_I\right] \sin2(\varphi-\psi_I)$$

$$= \frac{(P\_Y)}{\pi} + [\alpha]\cos2(\varphi-\psi_I) + [\beta]\sin2(\varphi-\psi_I)$$

$$= \frac{(P\_Y)}{\pi} + \sqrt{\alpha^2+\beta^2}\cos(2(\varphi-\psi_I-\gamma))$$

where P_Y is the intensity variation portion represented by Equation (10) and α and β are supposed to be as follows:

$$\alpha = \begin{bmatrix} a_0\frac{\pi(A+B)}{8} + a_2\frac{\pi(A-B)}{8}\cos2\psi_I + b_2\frac{\pi(A-B)}{8}\sin2\psi_I + \\ a_4\frac{\pi(A+B)}{16}\cos4\psi_I + b_4\frac{\pi(A+B)}{16}\sin4\psi_I \end{bmatrix} \quad (13)$$

$$\beta = \begin{bmatrix} -a_2\frac{\pi(A-B)}{8}\sin2\psi_I + b_2\frac{\pi(A-B)}{8}\cos2\psi_I - \\ a_4\frac{\pi(A+B)}{16}\sin4\psi_I + b_4\frac{\pi(A+B)}{16}\cos4\psi_I \end{bmatrix}$$

In these expressions of α and β, the values of the three variables a0, a2 and b2 are obtained from the intensity variation observation represented by Equation (9). Thus, the other two unknowns a4 and b4 can be determined by observing $\psi_I$ twice or more.

As can be seen from these considerations, if energy reflectance coefficient are supposed in two orthogonal directions of the grooves as polarization based super-resolution, then the distribution of the grooves' azimuth angles within a single pixel can be estimated. More specifically, by observing the intensity variation and polarized light intensity variation in a situation where plane polarized light is incident with the angle $\psi_I$ changed, the distribution function of the grooves within a single pixel can be estimated as the coefficients a0, a2, b2, a4 and b4 of the Fourier series expansion. If only the intensity variation is observed, a0, a2 and b2 can be estimated. By observing the polarized light intensity, the coefficients a4 and b4 can also be estimated. However, no more coefficients can be estimated. Consequently, the distribution of the azimuth angles of the grooves can be estimated symmetrically with respect to a half period π.

Figure 20:
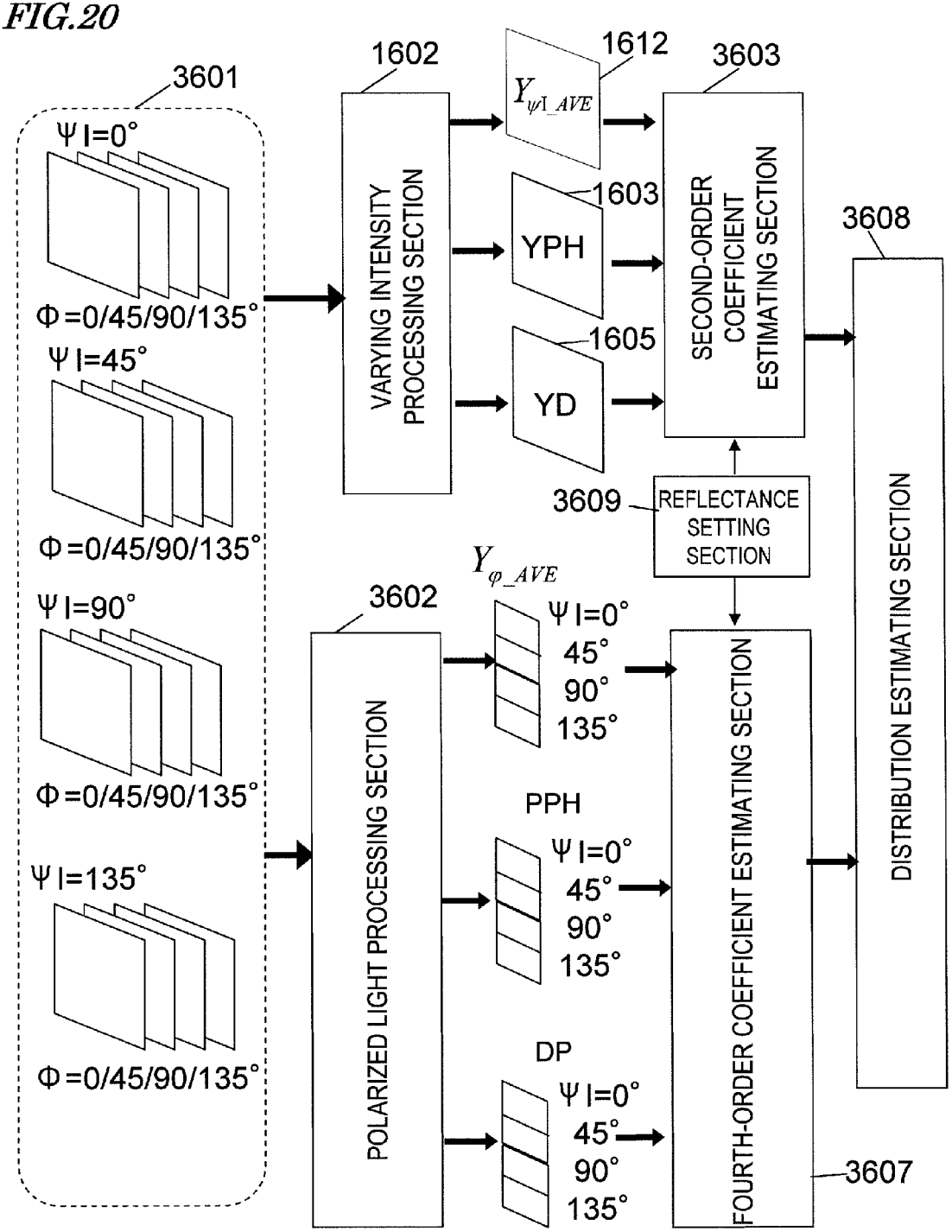
FIG. 20 is a diagram illustrating a configuration for an image processing processor according to the first embodiment of the present disclosure.

FIG. 20 is a block diagram illustrating an exemplary configuration for the image processing processor 3002.

By changing the plane of polarization angles ψI of the light from 0 degrees into 45, 90 and 135 degrees and capturing images of the object by illuminating the object with such light, a group 3601 of sixteen polarized light intensity images with φ set to be 0, 45, 90 and 135 degrees is obtained.

The reflectance setting section 3609 sets in advance the numerical values of A and B representing the energy reflectances in the groove principal axis direction, which depends on the object's material property such as the refractive index, and in the direction that intersects with the former direction at right angles. These numerical A and B values are what has already been described with reference to FIG. 13. For example, supposing the refractive index NN=1.8 and the groove tilt angle is 45 degrees, A and B may be set to be 0.05 and 0.2, respectively, according to the Fresnel theory.

The group 3601 of polarized light intensity images is input to the varying intensity processing section 1602, which obtains a non-polarized light average light intensity image 1612, an intensity maximizing angle image 1603 and a degree of intensity modulation image 1605 by making the calculations to be described below.

As described above, the intensity variation in a situation where the plane of polarization of polarized light is rotated becomes a cosine function with a period of 180 degrees. The varying intensity, processing section 1602 fits the intensity variation to the cosine function. Y(ψI) representing the intensity variation can be given by the following Equation (14) using the angle ψI of the plane of polarization of the light as a variable:

$$Y(\psi_I) = Y_{\psi I\_ave} + A_I \cos(2(\psi_I - \psi_0)) \quad (14)$$

Figure 21:
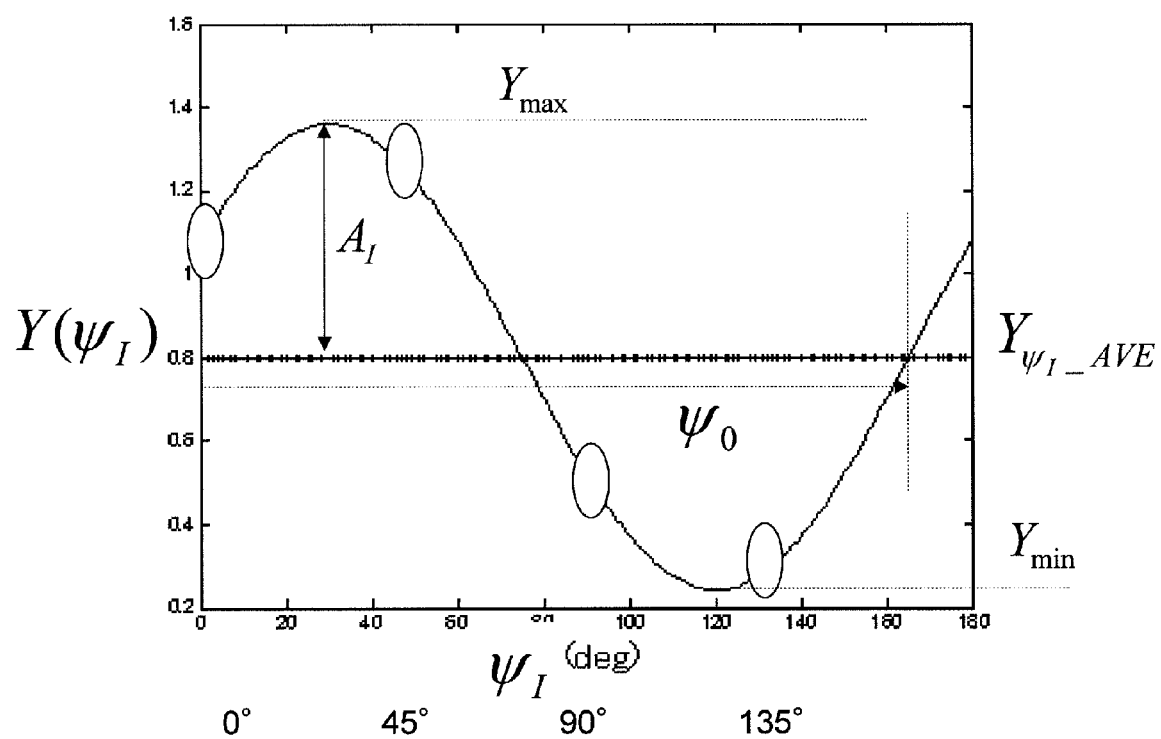
FIG. 21 shows how to make cosine function fitting based on samples of the polarized light intensities of four different kinds of polarized light sources.

FIG. 21 shows the cosine function of this intensity variation and indicates the meanings of the amplitude AI, the phase $\psi_o$ and the average $Y_{\psi I\_ave}$ described above. The four sample points are plotted right on that cosine function for the sake of simplicity.

These values can be estimated by fitting the cosine function based on the four angular samples that have been obtained at regular intervals in the following manner. First of all, the intensity $Y_{\psi I\_ave}$ of the original image under non-polarized light is calculated by the following Equation (15). The right side of this Equation (15) means adding together, and calculating the average of, four light intensity images that have been obtained from an object that is illuminated with polarized light at angles ψI of 0, 45, 90 and 135 degrees, respectively. The intensity $Y_{\psi I\_ave}$ approximately reproduces a light intensity image under non-polarized light and can be used as a normally observed image for an endoscope. That is why the intensity $Y_{\psi I\_ave}$ can be referred to herein as a "non-polarized light average light intensity image".

$$Y_{\psi I\_AVE} = \frac{1}{4}(Y(\psi_I=0°) + Y(\psi_I=45°) + Y(\psi_I=90°) + Y(\psi_I=135°)) \quad (15)$$

$$\approx \frac{1}{2}(Y_{max} + Y_{min})$$

Next, optimum fitting from the sampled intensities to the cosine function is carried out using a minimum mean square error. In this case, the optimum fitting process is begun by carrying out sampling in the four directions that are defined by 0, 45, 90 and 135 degrees, respectively. Since the cosine function is determined by the three kinds of information that are amplitude, phase and average, the number of samples for use to determine the cosine function does not have to be four but may actually be any other number as long as the number is at least three. Nevertheless, if samples are taken at a regular interval of 45 degrees in this manner, the optimum fitting can be simplified.

First of all, the square error E of the intensities at the polarization angles of 0, 45 (=π/4), 90 (=π/2) and 135 (=3 π/4) degrees is defined by the following Equation (16):

$$E = (Y(\psi_I = 0) - I_0)^2 + \left(Y\left(\psi_I = \frac{\pi}{4}\right) - I_1\right)^2 + \left(Y\left(\psi_I = \frac{\pi}{2}\right) - I_2\right)^2 + \left(Y\left(\psi_I = \frac{3\pi}{4}\right) - I_3\right)^2 \quad (16)$$

$$= (Y_{\psi I\_AVE} + A_I \cos(2\psi_O) - I_0)^2 + (Y_{\psi I\_AVE} + A_I \sin(2\psi_O) - I_1)^2 +$$
$$(Y_{\psi I\_AVE} - A_I \cos(2\psi_O) - I_2)^2 + (Y_{\psi I\_AVE} - A_I \sin(2\psi_O) - I_3)^2$$

The phase $\psi_o$ of the cosine function that minimizes this square error can be calculated by the following Equation (17):

$$\frac{\partial E}{\partial \psi_O} = 4A_I[(I_3 - I_1)\cos(2\psi_O) + (I_0 - I_2)\sin(2\psi_O)] = 0 \quad (17)$$

Based on this equation, the solutions can be given by the following Equations (18) and (19):

$$\begin{cases} \psi_O^{(+)} = \frac{1}{2}\cos^{-1}\left(\sqrt{\frac{c^2}{a^2 + c^2}}\right) \\ \psi_O^{(-)} = \frac{1}{2}\cos^{-1}\left(-\sqrt{\frac{c^2}{a^2 + c^2}}\right) \end{cases} \quad (18)$$

$$\begin{cases} a \equiv (I_3 - I_1) \\ c \equiv (I_0 - I_2) \end{cases} \quad (19)$$

A mathematical function such as an inverse trigonometric function generally imposes the following constraint:

$$0 \leq a \cos(x) \leq \pi \quad (20)$$

Considering this angular range, by making classification based on the magnitudes of a and c, the respective angles at which the maximum and minimum values are obtained can be calculated by the following Equations (21):

$$\begin{cases} \text{if } a < 0 \text{ and } c > 0, & \psi_{Omin} = \frac{\pi}{2} + \psi_O^{(+)} & \psi_{Omax} = \psi_O^{(+)} \\ \text{if } a < 0 \text{ and } c < 0, & \psi_{Omin} = \frac{\pi}{2} + \psi_O^{(-)} & \psi_{Omax} = \psi_O^{(-)} \\ \text{if } a > 0 \text{ and } c < 0, & \psi_{Omin} = \psi_O^{(+)} & \psi_{Omax} = \frac{\pi}{2} + \psi_O^{(+)} \\ \text{if } a > 0 \text{ and } c > 0, & \psi_{Omin} = \psi_O^{(-)} & \psi_{Omax} = \frac{\pi}{2} + \psi_O^{(-)} \end{cases} \quad (21)$$

The ψ0max value at which the maximum value is obtained can be used as it is as the intensity maximizing angle image 1603:

$$YPH = \psi_{Omax} \quad (22)$$

Next, the maximum and minimum values of the amplitude are obtained. First of all, to obtain the amplitude $A_I$, the square error is minimized by the following Equations (23) and (24):

$$\frac{\partial E}{\partial A_I} = 0 \quad (23)$$

$$A_I = \frac{1}{2}[(I_0 - I_2)\cos(2\psi_O) - (I_3 - I_1)\sin(2\psi_O)] \quad (24)$$

Using the amplitude $A_I$, the maximum and minimum values of the amplitude are calculated by the following Equations (25):

$$Y_{max} = Y_{\psi I\_AVE} + A_I$$
$$Y_{min} = Y_{\psi I\_AVE} - A_I \quad (25)$$

Thus, if the maximum and minimum values Ymax and Ymin of the amplitude given by these Equations (25) are applied as MAX and MIN to Equation (7), the degree of intensity modulation image 1605 can be obtained.

Normal optimum fitting to a cosine function can be carried out on three or more samples and its method is disclosed in Japanese Patent Publication No. 4235252, for example.

By performing these processing steps, the intensity maximizing angle image 1603 and the degree of intensity modulation image 1605 can be obtained. In FIG. 20, the intensity maximizing angle image 1603 and the degree of intensity modulation image 1605 are identified by the reference signs YPH and YD, respectively. As shown in FIG. 20, the intensity maximizing angle image YPH and the degree of intensity modulation image YD are passed to a second-order coefficient estimating section 3603.

In this manner, the varying intensity processing section 1602 deals with an intensity variation involved with a variation in the plane of polarization angle ΨI of the illumination irrespective of observation of polarized light.

The second order coefficient estimating section 3603 calculates a Fourier expansion coefficient by Equation (9) using the intensity maximizing angle image 1603 and the degree of intensity modulation image 1605 that have been obtained by processing the intensity variation.

First of all, the second order coefficient estimating section 3603 calculates the average intensity 1612 in the same way as in Equation (15). That is to say, by using only a polarized light source as the illumination and by adding together, and calculating the average of, the light intensity images that have been captured with the plane of polarization rotated, a light intensity image under a non-polarized light source can be reproduced approximately. Thus, there is no need to switch the illuminating light between a normal observation mode and a polarized light observation mode, thus enabling the image processing processor to perform both of these functions. And these functions can be performed no matter whether the image is a monochrome one or a colored one. Consequently, a color light intensity image can be obtained under a normal non-polarized white light source. Furthermore, based on this average intensity 1612, i.e., $Y_{\psi I\_ave}$, the expansion coefficient a0 can be obtained by the following Equation (26):

$$a_0 = \frac{Y_{\psi I\_ave}}{\left(\frac{(A+B)\pi^2}{4}\right)} = \frac{4Y_{\psi I\_ave}}{(A+B)\pi^2} \quad (26)$$

Using Ψ0 obtained by Equation (9) (i.e., the intensity maximizing angle image 1603 (YPH) that has been obtained by the varying intensity processing section 1602) and the average intensity 1612 ($Y_{\psi I\_ave}$), a2 and b2 can be calculated by $$\therefore a_2 = \begin{cases} +DP \cdot Y_{\psi I\_ave} \cdot \left(\frac{8}{(A-B)\pi^2}\right) \frac{1}{\sqrt{1+tan^2 2\psi_0}} L & (27) \\ \left(0 < \psi_0 < \frac{\pi}{4}, \frac{3\pi}{4} < \psi_0 < \frac{5\pi}{4}, \frac{7\pi}{4} < \psi_0\right) \\ -DP \cdot Y_{\psi I\_ave} \cdot \left(\frac{8}{(A-B)\pi^2}\right) \frac{1}{\sqrt{1+tan^2 2\psi_0}} L \\ \left(\frac{\pi}{4} < \psi_0 < \frac{3\pi}{4}, \frac{5\pi}{4} < \psi_0 < \frac{7\pi}{4}\right) \end{cases}$$

$$\therefore b_2 = a_2 \tan 2\psi_0$$

Only these expansion coefficients can be obtained by observing the intensity variation. To obtain a4 and b4, on the other hand, polarized light needs to be observed.

The polarized light processing section 3602 performs optimum fitting of $\phi$ under a fixed light source to the intensity variation cosine function for samples at 0, 45, 90 and 135 degrees. It is well known that when a polarized light transmission plane is rotated, an intensity variation generally becomes a cosine function with a period of 180 degrees (see Japanese Laid-Open Patent Publication No. 2007-86720, for example). Supposing the angle of the plane of polarization to observe is $\phi$, fitting can be made in the following manner:

$$Y(\phi) = Y_{\phi\_ave} + A_I \cos(2(\phi - \gamma)) \quad (28)$$

This function includes three kinds of information about amplitude, phase and average.

Figure 22:
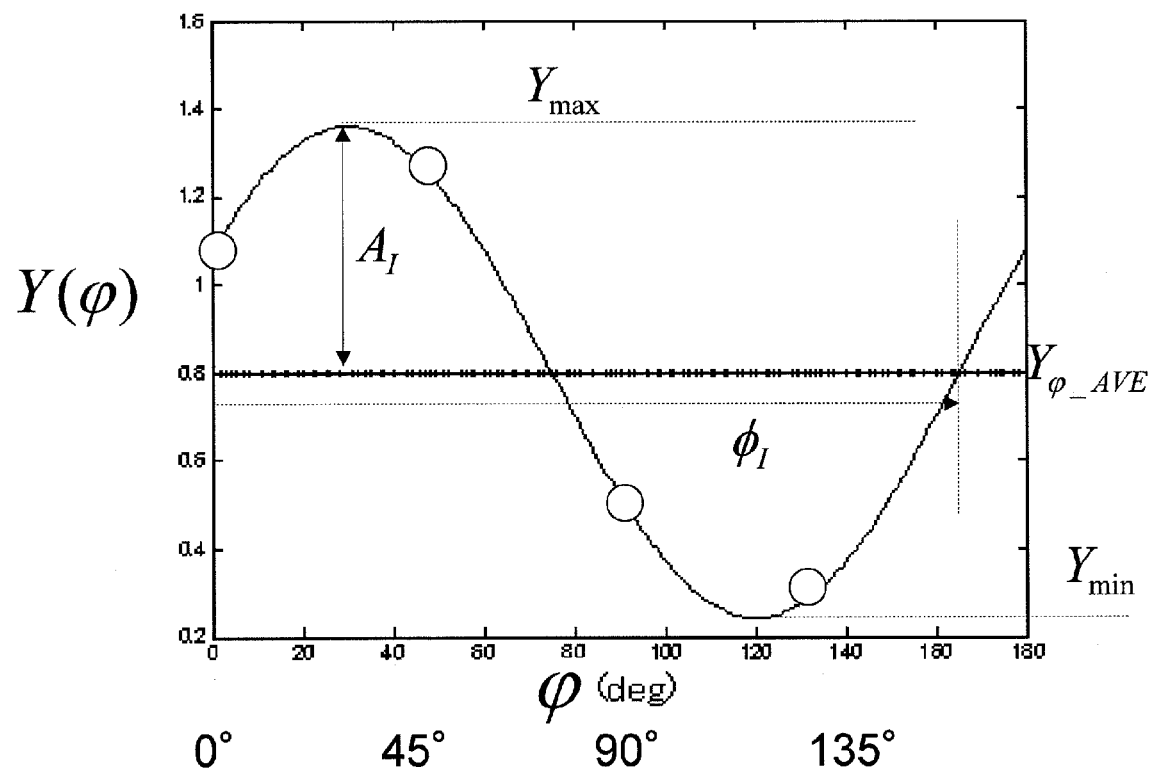
FIG. 22 shows how to make cosine function fitting based on samples of the polarized light intensities at four different kinds of polarized light observation angles.

FIG. 22 shows the cosine function of this intensity variation and indicates the meanings of the amplitude, phase and average described above. The four sample points are plotted right on that cosine function for the sake of simplicity. Since the specific procedure of estimating these values by making fitting to a cosine function using four angular samples that are plotted at regular intervals is the same as in making fitting for the intensity variation, description thereof will be omitted herein.

First of all, the average intensity $Y_{\phi\_ave}$ is calculated by the following Equation (29). This average of the sum corresponds to a light intensity image obtained by calculating the average of the polarized light images under a polarized light source with an angle $\psi I$. This image will be referred to herein as an average intensity image 3610.

$$Y_{\varphi\_AVE} = \frac{1}{4}(Y(\varphi = 0°) + Y(\varphi = 45°) + Y(\varphi = 90°) + Y(\varphi = 135°)) \quad (29)$$

$$\approx \frac{1}{2}(Y_{max} + Y_{min})$$

The polarized light maximizing angle image PPH is generated by regarding the $\phi 0$ value that maximizes Equation (12) as the polarized light maximizing angle image PPH as it is.

The degree of polarization image (DP) 3606 is generated by Equation (8) using the maximum and minimum values of Equation (12).

The average intensity image $Y_{\phi\_ave}$ 3610, the polarization maximizing angle image PPH 3604, and the degree of polarization image DP 3606 are all determined on the basis of the angle of the polarized light source $\psi I$. That is why in the example shown in FIG. 20, each of these images consists of four pictures that are associated with the respective angles of the light source.

The fourth order estimating section 3607 estimates the expansion coefficients a4 and b4 based on these images.

First of all, the angle of the polarization maximizing angle image PPH is supposed to be $\gamma$. Meanwhile, the DP image has the original DP value as it is. In that case, the following relations are satisfied:

$$\tan 2\gamma = \frac{\beta}{\alpha} \quad (30)$$

$$DP = \frac{\sqrt{\alpha^2 + \beta^2}}{Y_{\varphi\_ave}}$$

That is to say, $\alpha$ and $\beta$ can be calculated by the following Equation (31) using the $Y_{\phi\_ave}$, $\gamma$ and DP values.

$$\alpha = \begin{cases} -\frac{DP \cdot Y_{\varphi\_ave}}{\sqrt{1+tan^2 2\gamma}} & \left(\frac{\pi}{4} < \phi < \frac{3\pi}{4}, \frac{5\pi}{4} < \phi < \frac{7\pi}{4}\right) \\ \frac{DP \cdot Y_{\varphi\_ave}}{\sqrt{1+tan^2 2\gamma}} & (else) \end{cases} \quad (31)$$

$$\beta = \alpha \cdot \tan 2\gamma$$

In this case, replacement is made in the following manner based on Equation (9):

$$\begin{bmatrix} \alpha\alpha \\ \beta\beta \end{bmatrix} = \frac{16}{A+B} \begin{bmatrix} \frac{\alpha}{\pi} - \left(\frac{(A+B)}{8}a_0 + a_2\frac{(A-B)}{8}\cos 2\psi_I + b_2\frac{(A-B)}{8}\sin 2\psi_I\right) \\ \frac{\beta}{\pi} - \left(-a_2\frac{(A-B)}{8}\sin 2\psi_I + b_2\frac{(A-B)}{8}\cos 2\psi_I\right) \end{bmatrix} \quad (32)$$

As can be seen from the following Equations (33), the equation to be solved to obtain the expansion coefficients a4 and b4 becomes simultaneous equations with excessive constraints, and therefore, can be solved using a pseudo-inverse matrix. However, $\psi_{I0}$, $\psi_{I1}$, $\psi_{I2}$ and $\psi_{I3}$ mean 0, 45, 90 and 135 degrees, respectively.

$$\begin{bmatrix} \cos 4\psi_{I0} & -\sin 4\psi_{I0} \\ \sin 4\psi_{I0} & \cos 4\psi_{I0} \\ \cos 4\psi_{I1} & -\sin 4\psi_{I1} \\ \sin 4\psi_{I1} & \cos 4\psi_{I1} \\ \cos 4\psi_{I2} & -\sin 4\psi_{I2} \\ \sin 4\psi_{I2} & \cos 4\psi_{I2} \\ \cos 4\psi_{I13} & -\sin 4\psi_{I3} \\ \sin 4\psi_{I3} & \cos 4\psi_{I3} \end{bmatrix} \begin{bmatrix} a_4 \\ b_4 \end{bmatrix} = \begin{bmatrix} \alpha\alpha(\psi_{I0}) \\ \beta\beta(\psi_{I0}) \\ \alpha\alpha(\psi_{I1}) \\ \beta\beta(\psi_{I1}) \\ \alpha\alpha(\psi_{I2}) \\ \beta\beta(\psi_{I2}) \\ \alpha\alpha(\psi_{I13}) \\ \beta\beta(\psi_{I13}) \end{bmatrix} \quad (33)$$

$$A \begin{bmatrix} a_4 \\ b_4 \end{bmatrix} = B$$

$$\begin{bmatrix} a_4 \\ b_4 \end{bmatrix} = (A^t A)^{-1} A^t B$$

Figure 23A:
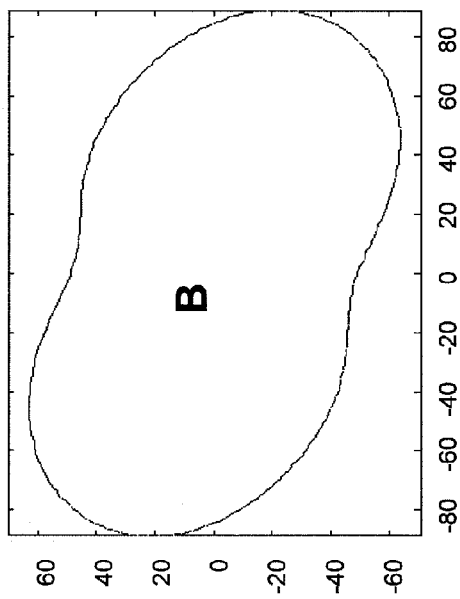
FIG. 23A shows the distributions of surface grooves' azimuth angles in a single pixel, which were obtained in an embodiment of the present disclosure.
Figure 23A:
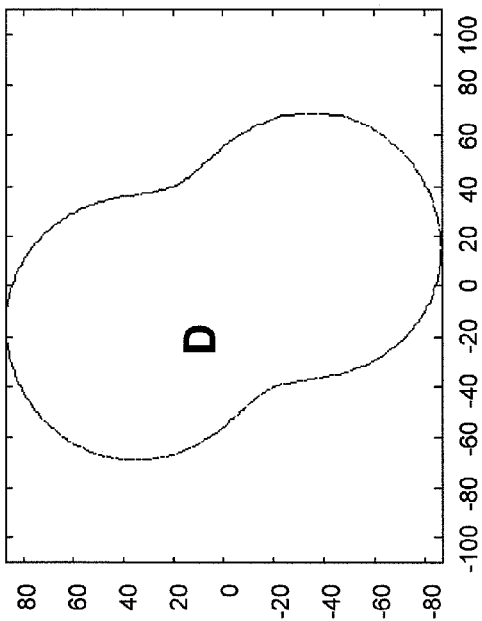
Figure 23A:
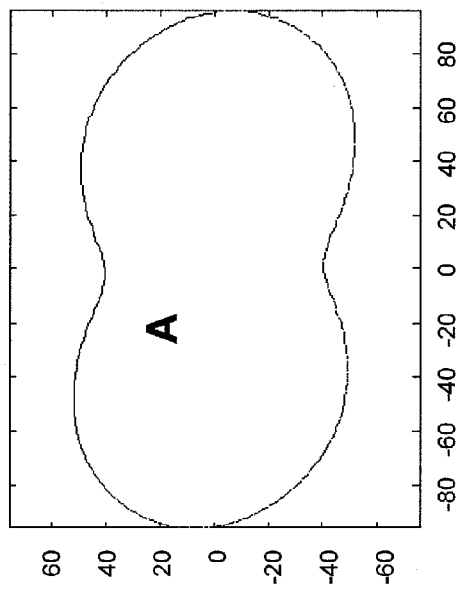
Figure 23A:
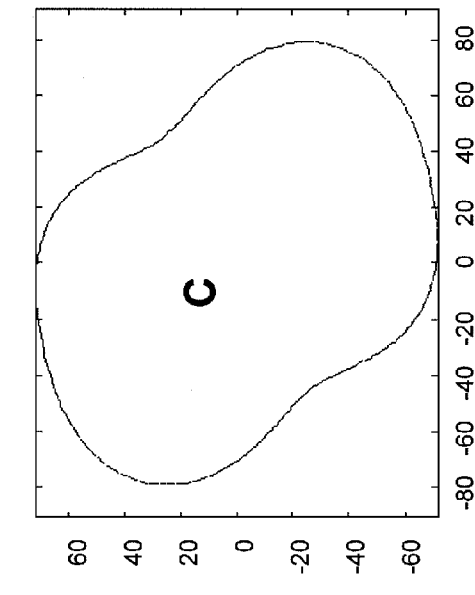
Figure 23B:
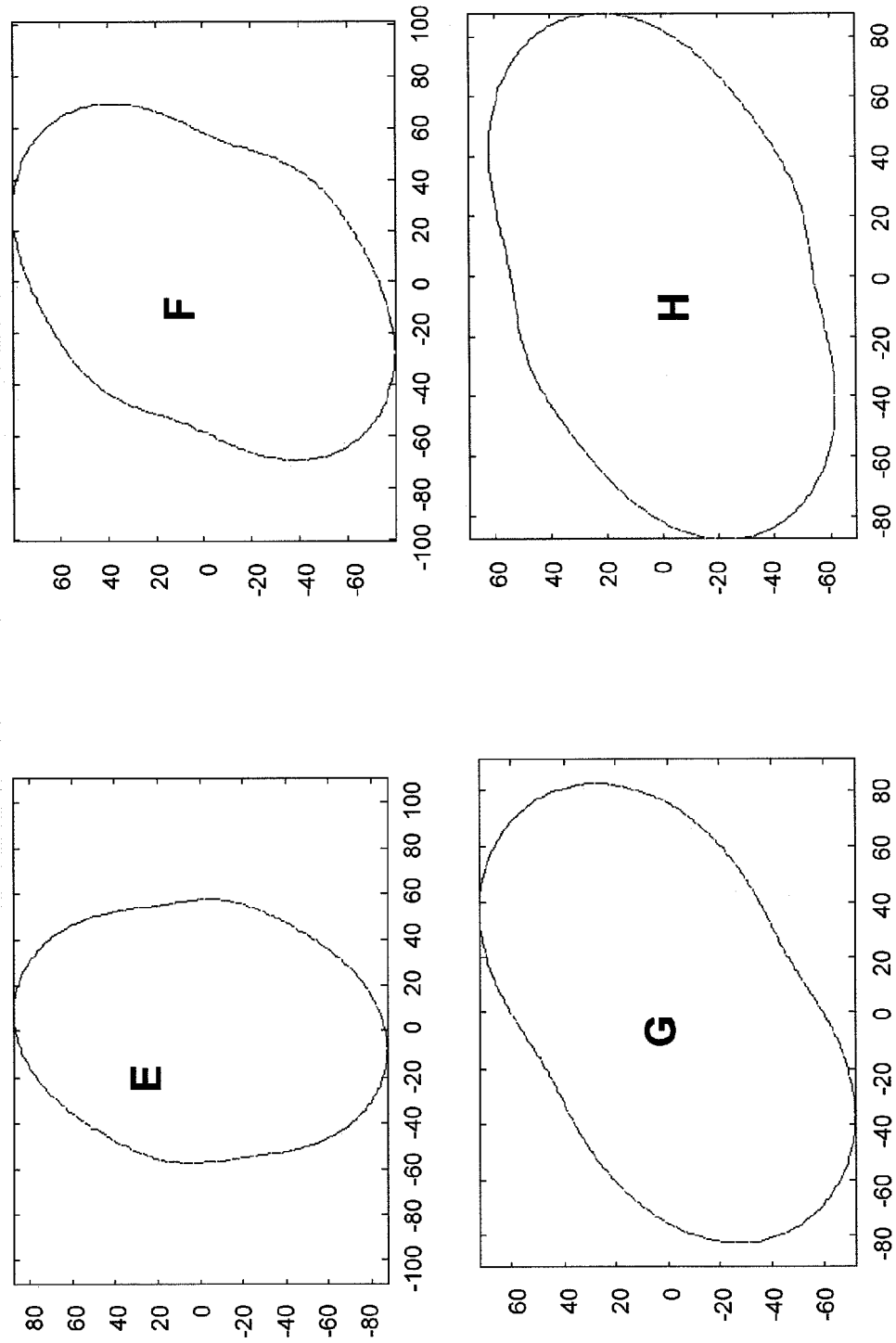
FIG. 23B shows the distributions of surface grooves' azimuth angles in a single pixel, which were obtained in an embodiment of the present disclosure.

FIGS. 23A and 23B show the results of experiments in which the distribution of the azimuth angles of normals within a single pixel was actually obtained using the Fourier expansion coefficients that had been obtained as described above. The object was supposed to be a single pixel that was present inside the grooves A through H of the object shown in FIGS. 24A and 24B and rendering was carried out with the expansion coefficients substituted into Equation (1).

Figure 24A:
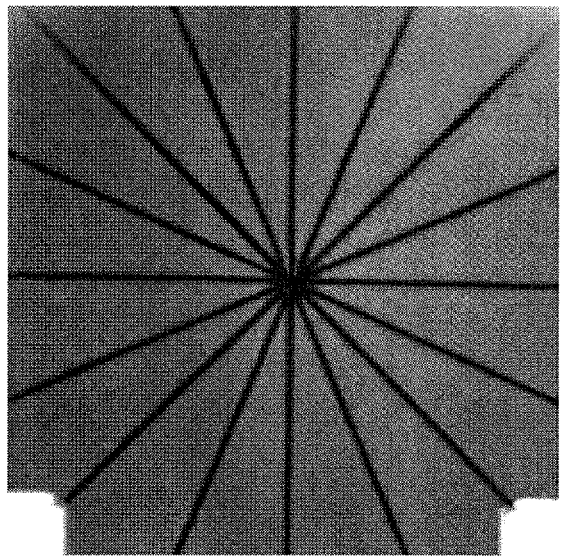
FIG. 24A illustrates, as an example, a stellar object with grooves.
Figure 24B:
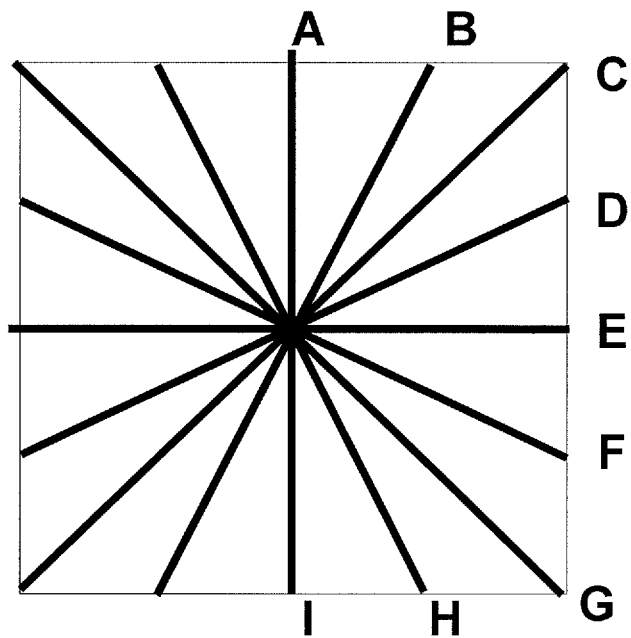
FIG. 24B schematically illustrates the object shown in FIG. 25A.

FIG. 24 shows that object, which is a plastic plate through which eight grooves A through I were cut and which was painted. Specifically, FIG. 24A is a photograph showing a light intensity image that was obtained by shooting the real object and FIG. 24B is a schematic representation thereof. Two adjacent grooves within this plane had an azimuth angle interval of 22.5 degrees.

The following Table 1 shows the expansion coefficients that were obtained at respective groove positions. As can be seen from FIGS. 23A and 23B, the principal axes of the distributions of the grooves A through H rotate gradually. Even though there should be no direct correlation between the principal axis of the distribution of a groove within a single pixel and the direction of a macroscopic groove, the principal axis of the distribution of normals still turned out to be present on the slope direction of the groove.

TABLE 1

| Pixel position (groove) | Coefficient a0 | Coefficient a2 | Coefficient a4 | Coefficient b2 | Coefficient b4 |
| --- | --- | --- | --- | --- | --- |
| A | 69.708975 | 27.466445 | 2.558916 | −1.503381 | 2.267980 |
| B | 69.708975 | 17.949969 | 13.525970 | −2.808555 | 2.072687 |
| C | 71.330113 | −0.297917 | 14.392751 | 1.252213 | 5.048574 |
| D | 66.466697 | −14.457502 | 17.691217 | 0.394808 | 2.233250 |
| E | 63.224419 | −14.633930 | −3.666218 | 2.366086 | 2.647317 |
| F | 63.224419 | −7.485956 | −14.400412 | −4.080576 | 0.712994 |
| G | 64.845558 | 7.731021 | −19.018256 | −4.723332 | 1.151819 |
| H | 72.951252 | +13.913825 | −12.885530 | −1.478054 | −3.972120 |

By combining this super-resolution method with the first embodiment, even for surface micro-geometry, of which the resolution could not be obtained because it would be a single pixel just by observing the intensity, the distribution of the directions (azimuth angles) of the grooves that are present on the surface can also be estimated and presented as an image by using polarized light, which is very much beneficial. In addition, besides observing an endoscope image with high definition, this technique is also applicable as an aid for making a diagnosis based on an endoscope image by using the expansion coefficients obtained in this embodiment as a feature quantity for classifying and recognizing the pattern of the objects' surfaces based on the statistical quantities of the grooves.

Embodiment 2

Figure 25:
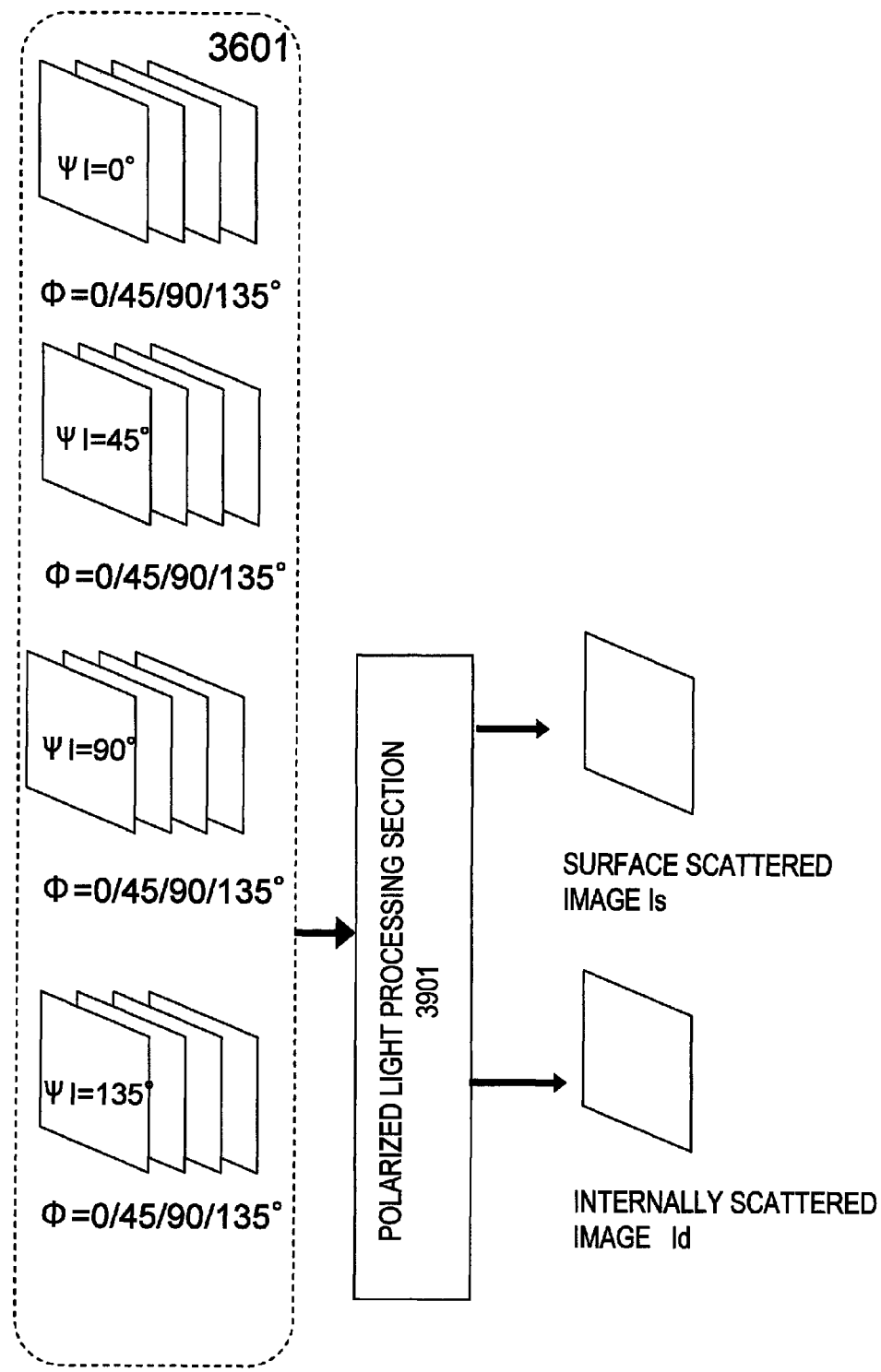
FIG. 25 illustrates a configuration for an image processing processor as a second embodiment of the present disclosure.

FIG. 25 illustrates a second embodiment of the present disclosure and shows a portion of the image processing processor 3002 shown in FIG. 1C. According to this embodiment, the incoming light can be separated into light scattered from the surface of an organ and light scattered from a depth of a tissue. In this embodiment, the polarized light processing section 3602 shown in FIG. 20 is replaced with a polarized light processing section 3901 shown in FIG. 25, which is a difference from the configuration of the first embodiment.

In many cases, traditional polarization endoscopes are designed mainly for the purpose of obtaining a high contrast image by separating the light scattered from the surface of an organ from the light scattered from a depth of a tissue. In that case, a P wave is used as a polarized light source and an S wave is used to observe an image. That is to say, polarized light that is polarized in a predetermined direction needs to be used and another polarized light, of which the polarization direction is perpendicular to the former direction, needs to be observed. According to the traditional technology, however, illuminating methods are quite different between a polarization shooting mode in which a polarized light source and a polarization image captured are used in combination and a normal color shooting mode in which non-polarized light is used. That is why the endoscope itself should have a mechanism for changing the illuminating devices. On top of that, if the same optical system is used in common to shoot a polarization image and a normal color image, the wavelength range in which the polarization image can be shot should be separated from the wavelength range in which the normal image can be shot. Consequently, in the common wavelength range of 380 nm to 780 nm, it has been difficult to carry out both the normal color shooting and the polarization image capturing at the same time. On the other hand, the image processing apparatus of this embodiment includes a light source that rotates the plane of polarization and a polarization image sensor, and therefore, can carry out easily both the normal color shooting and the polarization image capturing.

As in the first embodiment described above, the plane of polarization angles ψI of the light source are also changed according to this embodiment from 0 degrees into 45, 90 and 135 degrees sequentially, and a group 3601 of sixteen polarized light intensity images, which have been captured under such a light source at 0, 45, 90 and 135 degrees, are input. That is why this embodiment provides a variety of combinations in which the polarization direction of the light source is perpendicular to the polarization direction for observation (i.e., the direction of the polarized light transmission axis). For example, suppose ψI=0 degrees is selected and four kinds of polarization images, of which φ are 0, 45, 90 and 135 degrees, respectively, are used under this light source. Using those polarization images, the four polarized light intensities at each pixel can be regarded as the four sample points indicated by the open circles in FIG. 22. And those four polarized light intensities are fit to a cosine function. Based on a curve thus obtained to represent the relation between the polarized light intensity and the polarized light transmission axis, Ymax and Ymin shown in FIG. 22 are determined. By using Ymax and Ymin thus obtained, the surface scattered light Is and internally scattered light Id can be calculated by the following Equations (34) and those images can be obtained.

$$Is = Y\max - Y\min$$

$$Id = 2Y\min \qquad (34)$$

According to this embodiment, the surface scattered light Is and the internally scattered light Id can be separated from each other without adding any special mechanism to the apparatus of the first embodiment. If the polarization image sensor is a colored one, then the intensities described above may be processed as respective color components. In that case, a normal non-polarized color image is obtained by Equation (29) and a color image in the same wavelength range, of which the components have been separated using polarized light, is obtained by Equation (34).

The polarized light source angle ψI can be freely changed from 0 degrees into any other value. That is why it can be calculated what result will be obtained when observation is carried out by using the direction that is perpendicular to that polarization direction as the polarized light transmission axis at an arbitrary polarized light source angle ψI.

For example, intensity variations in a situation where the polarization observation angle φ is fixed at 0 degrees and where the polarized light source angle ψI is changed from 0 degrees into 45, 90 and 135 degrees may be used.

Embodiment 3

Hereinafter, a third embodiment of an image processing apparatus according to the present disclosure will be described with reference to FIGS. 26A and 26B. The image processing apparatus of this embodiment is applicable to not only an endoscope but also a camera with illumination for medical purposes (which may be used in a dermatologist's or a dentist's), a fingerprint scanner, an optical surface analyzer and other devices.

Figure 26A:
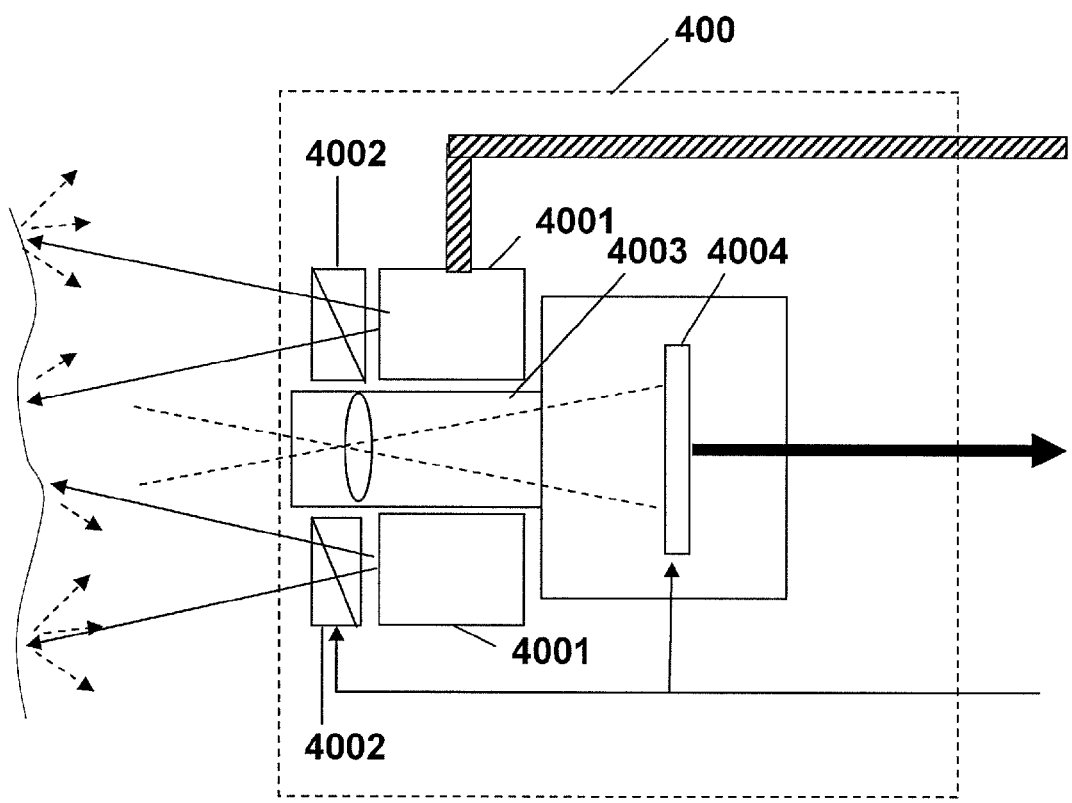
FIG. 26A illustrates a configuration according to a third embodiment of the present disclosure.

FIG. 26A illustrates an exemplary configuration according to this embodiment. The image processing apparatus of this embodiment uses a device 400 instead of the endoscope 101 shown in FIG. 1C. The device 400 includes a ring light 4001, a ring plane of polarization control element 4002, a shooting lens 4003 and an image sensor 4004.

Figure 26B:
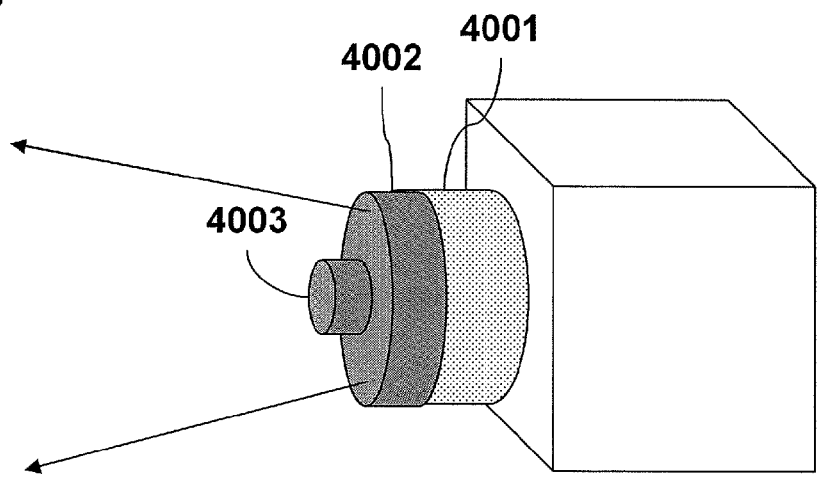
FIG. 26B illustrates the appearance of the third embodiment of the present disclosure.

FIG. 26B illustrates a general appearance of the device shown in FIG. 26A. In this embodiment, the ring plane of polarization control element 4002 is arranged on the ring light 4001. A non-polarized light ray is input through a light guide such as an optical filter to the ring light 4001 and the plane of polarization control element 4002 and has its plane of polarization rotated in the order of 0, 45, 90 and 135 degrees as shown in FIG. 2.

Alternatively, the ring light 4001 may also be a self-emitting light source such as an LED without using such a light guide that propagates the light emitted from a light source. Also, if the angle defined by the optical axis of the image sensor with respect to that of the illuminating light is 15 degrees or less, the ring light may also be replaced with a strobe light. However, if the ring light is used, even an object that would be hard to observe with only one light can also have its surface micro-geometry and grooves estimated with high precision. Among other things, in that case, since the optical axis of the illuminating light can be substantially aligned with that of the image sensor and can also be uniform, this device can be used effectively as a device for scanning the surface of a product for any scratches or checking its micro-geometry, a fingerprint scanner, or a skin unevenness checker for a dermatologist. As for the image sensor 4004 and the image processing processor (not shown), the image processing processor of the first embodiment can be used.

In the embodiment described above, the plane polarized light as the light source is supposed to be rotated on a 45-degree-a-time basis. However, the angle of rotation does not have to be the same, but may be changed, each time. On top of that, the angular interval does not have to be 45 degrees, either. Nevertheless, in order to determine three parameters for a cosine function, at least three samples are needed. That is to say, as for plane polarized light as a light source, its angle of rotation should be changed into three or more different values. For example, if three sample angles are used, the three angles of 0, 60 and 120 degrees may be selected, for example.

The present disclosure is broadly applicable to the field of image processing that needs observing, checking, or recognizing the object's surface micro-geometry using a medical endoscope camera, a medical camera for dermatologists, dentists, internists or surgeons, an industrial endoscope camera, a fingerprint scanner, or an optical surface analyzer.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An image processing apparatus comprising:
a polarized light source which sequentially illuminates an object with three or more kinds of plane polarized light rays, of which the planes of polarization have mutually different angles;
a polarization image sensor which sequentially captures an image of the object that is being illuminated with each of the three or more kinds of plane polarized light rays and which obtains a plurality of polarization images by sequentially changing the direction of the polarized light transmission axis into three or more different ones at each pixel while the object is being illuminated with each of the three or more kinds of plane polarized light rays;
a varying intensity processing section which obtains a relation between the angle of the plane of polarization and the intensity value of each pixel based on a pixel signal supplied from the polarization image sensor, thereby generating an intensity maximizing angle image that is defined by the angle of the plane of polarization that maximizes the intensity value with respect to each said pixel and a degree of intensity modulation image that is defined by the ratio of the amplitude of variation in the intensity value caused by the change of the plane of polarization to an average intensity value with respect to each said pixel; and
a distribution estimating section which estimates, based on the intensity maximizing angle image and the degree of intensity modulation image, the distribution in a single pixel of the azimuth angles of V-grooves on the object's surface.

2. The image processing apparatus of claim 1, wherein the intensity value is obtained by adding together a plurality of polarized light intensities which have been obtained by sequentially changing the direction of the polarized light transmission axis into three or more different ones at each pixel while the object is being illuminated with each of the plane polarized light rays and by calculating their average on a pixel-by-pixel basis, and wherein the intensity value varies with the angle defined by the plane of polarization of the plane polarized light of the polarized light source.

3. The image processing apparatus of claim 2, further comprising a polarized light processing section which generates, with respect to each angle defined by the plane of polarization of the polarized light source in each said pixel, a polarization maximizing angle image that is defined by the direction of the polarized light transmission axis that maximizes the polarized light intensity of the polarization image sensor, and a degree of polarization image that is defined by the ratio of the amplitude of the variation in the polarized light intensity as the direction of the polarized light transmission axis changes in each said pixel to the average of the polarized light intensities, and wherein the distribution estimating section increases the accuracy of estimation of the distribution of azimuth angles based on the polarization maximizing angle image and the degree of polarization image.

4. The image processing apparatus of claim 3, wherein the distribution estimating section includes:

a first coefficient estimating section which estimates, based on the output of the varying intensity processing section, zero- and second-order expansion coefficients to make a Fourier transform of a function representing the distribution of azimuth angles of the V-grooves; and a second coefficient estimating section which estimates, based on the output of the polarized light processing section, the fourth-order expansion coefficient to make a Fourier transform of the function.

* * * * *